(12) United States Patent
Say

(10) Patent No.: US 9,445,755 B2
(45) Date of Patent: Sep. 20, 2016

(54) ELECTROCHEMICAL SENSOR MODULE

(75) Inventor: James L. Say, Breckenridge, CO (US)

(73) Assignee: PEPEX BIOMEDICAL, LLC, Alameda, CA (US)

(*) Notice: Subject to any disclaimer, the term of this patent is extended or adjusted under 35 U.S.C. 154(b) by 813 days.

(21) Appl. No.: 13/129,343

(22) PCT Filed: Nov. 12, 2009

(86) PCT No.: PCT/US2009/064228
§ 371 (c)(1),
(2), (4) Date: Jul. 19, 2011

(87) PCT Pub. No.: WO2010/056878
PCT Pub. Date: May 20, 2010

(65) Prior Publication Data
US 2011/0270061 A1 Nov. 3, 2011

Related U.S. Application Data

(60) Provisional application No. 61/114,844, filed on Nov. 14, 2008.

(51) Int. Cl.
*A61B 5/00* (2006.01)
*A61B 5/15* (2006.01)
(Continued)

(52) U.S. Cl.
CPC ........... *A61B 5/1411* (2013.01); *A61B 5/1486* (2013.01); *A61B 5/157* (2013.01); *A61B 5/150022* (2013.01); *A61B 5/15132* (2013.01); *A61B 5/15155* (2013.01); *A61B 5/15174* (2013.01); *A61B 5/150213* (2013.01); *A61B 5/150358* (2013.01); *A61B 5/150396* (2013.01); *A61B 5/150503* (2013.01); *G01N 33/5438* (2013.01); *A61B 5/14532* (2013.01); *A61B 2560/0443* (2013.01)

(58) Field of Classification Search
None
See application file for complete search history.

(56) References Cited

U.S. PATENT DOCUMENTS 1,454,224 A   5/1923   Schmidt
2,291,720 A   8/1942   Hukle
(Continued)

FOREIGN PATENT DOCUMENTS

DE          101 12 384 A1    9/2002
DE    10 2004 060 742 A1    7/2006
(Continued)

OTHER PUBLICATIONS

European Search Report for 09826755.2 mailed Oct. 5, 2012.
(Continued)

*Primary Examiner* — Etsub Berhanu
*Assistant Examiner* — Karen Toth
(74) *Attorney, Agent, or Firm* — Merchant & Gould P.C.

(57) ABSTRACT

Certain embodiments of a sensor cartridge element include a sensor module, an electrode arrangement installed on the sensor module, and a delivery arrangement securely coupled to the sensor module. The sensor module includes an analysis cell and a skin piercing member. The electrode arrangement generates an electrical signal when exposed to a fluid sample collected in the analysis cell. The delivery arrangement includes a drug reservoir, a piston chamber, and a valve arrangement providing selective fluid communication between the drug reservoir and the piston chamber. Metering electronics and an actuator can manage collection of fluid samples and/or dispensing of drug doses.

23 Claims, 25 Drawing Sheets

(51) Int. Cl.
  *A61B 5/1486* (2006.01)
  *G01N 33/543* (2006.01)
  *A61B 5/151* (2006.01)
  *A61B 5/157* (2006.01)
  *A61B 5/145* (2006.01)

(56) References Cited

U.S. PATENT DOCUMENTS

| | | |
|---|---|---|
| 3,170,968 A | 2/1965 | Rokunohe et al. |
| 3,823,035 A | 7/1974 | Sanders |
| 4,008,717 A | 2/1977 | Kowarski |
| 4,073,974 A | 2/1978 | Albarino et al. |
| 4,224,125 A | 9/1980 | Nakamura et al. |
| 4,255,487 A | 3/1981 | Sanders |
| 4,321,057 A | 3/1982 | Buckles |
| 4,399,099 A | 8/1983 | Buckles |
| 4,545,382 A | 10/1985 | Higgins et al. |
| 4,545,835 A | 10/1985 | Gusack et al. |
| 4,552,840 A | 11/1985 | Riffer |
| 4,573,968 A | 3/1986 | Parker |
| 4,640,821 A | 2/1987 | Mody et al. |
| 4,671,288 A | 6/1987 | Gough |
| 4,704,311 A | 11/1987 | Pickering et al. |
| 4,734,184 A | 3/1988 | Burleigh et al. |
| 4,820,399 A | 4/1989 | Senda et al. |
| 4,824,206 A | 4/1989 | Klainer et al. |
| 4,846,548 A | 7/1989 | Klainer |
| 4,880,752 A | 11/1989 | Keck et al. |
| 4,908,115 A | 3/1990 | Morita et al. |
| 4,919,649 A | 4/1990 | Timothy et al. |
| 4,927,516 A | 5/1990 | Yamaguchi et al. |
| 4,945,896 A | 8/1990 | Gade |
| 4,974,929 A | 12/1990 | Curry |
| 4,981,779 A | 1/1991 | Wagner |
| 5,001,054 A | 3/1991 | Wagner |
| 5,004,583 A | 4/1991 | Guruswamy et al. |
| RE33,677 E | 8/1991 | Vazirani |
| 5,047,044 A | 9/1991 | Smith et al. |
| 5,112,455 A | 5/1992 | Cozzette et al. |
| 5,131,138 A | 7/1992 | Crouse |
| 5,164,229 A | 11/1992 | Hay et al. |
| 5,165,406 A | 11/1992 | Wong |
| 5,165,407 A | 11/1992 | Wilson et al. |
| 5,171,689 A | 12/1992 | Kawaguri et al. |
| 5,186,808 A | 2/1993 | Yamaguchi et al. |
| 5,205,920 A | 4/1993 | Oyama et al. |
| 5,217,533 A | 6/1993 | Hay et al. |
| 5,220,920 A | 6/1993 | Gharib |
| 5,243,982 A | 9/1993 | Möstl et al. |
| 5,244,636 A | 9/1993 | Walt et al. |
| 5,250,264 A | 10/1993 | Walt et al. |
| 5,262,035 A | 11/1993 | Gregg et al. |
| 5,264,092 A | 11/1993 | Skotheim et al. |
| 5,264,103 A | 11/1993 | Yoshioka et al. |
| 5,264,104 A | 11/1993 | Gregg et al. |
| 5,264,105 A | 11/1993 | Gregg et al. |
| 5,269,891 A | 12/1993 | Colin |
| 5,271,815 A | 12/1993 | Wong |
| 5,271,820 A | 12/1993 | Kinlen et al. |
| 5,277,872 A | 1/1994 | Bankert et al. |
| 5,298,144 A | 3/1994 | Spokane |
| 5,298,741 A | 3/1994 | Walt et al. |
| 5,320,725 A | 6/1994 | Gregg et al. |
| 5,320,814 A | 6/1994 | Walt et al. |
| 5,330,634 A | 7/1994 | Wong et al. |
| 5,356,786 A | 10/1994 | Heller et al. |
| 5,366,527 A | 11/1994 | Amos et al. |
| 5,372,133 A | 12/1994 | Hogen Esch |
| D354,347 S | 1/1995 | Knute et al. |
| D354,559 S | 1/1995 | Knute et al. |
| 5,384,028 A | 1/1995 | Ito |
| 5,422,246 A | 6/1995 | Koopal et al. |
| 5,431,174 A | 7/1995 | Knute |
| 5,437,973 A | 8/1995 | Vadgama et al. |
| 5,503,728 A | 4/1996 | Kaneko et al. |
| 5,505,828 A | 4/1996 | Wong et al. |
| 5,512,159 A | 4/1996 | Yoshioka et al. |
| 5,575,403 A | 11/1996 | Charlton et al. |
| 5,593,852 A | 1/1997 | Heller et al. |
| 5,605,152 A | 2/1997 | Slate et al. |
| 5,609,749 A | 3/1997 | Yamauchi et al. |
| 5,645,710 A | 7/1997 | Shieh |
| 5,656,241 A | 8/1997 | Seifert et al. |
| 5,720,924 A | 2/1998 | Eikmeier et al. |
| 5,810,199 A | 9/1998 | Charlton et al. |
| 5,849,415 A | 12/1998 | Shalaby et al. |
| 5,863,800 A | 1/1999 | Eikmeier et al. |
| 5,900,215 A | 5/1999 | Seifert et al. |
| 5,951,764 A | 9/1999 | Hay et al. |
| 5,971,941 A | 10/1999 | Simons et al. |
| 5,972,199 A | 10/1999 | Heller et al. |
| 5,982,959 A | 11/1999 | Hopenfeld |
| 5,997,501 A | 12/1999 | Gross et al. |
| 6,036,924 A | 3/2000 | Simons et al. |
| 6,044,665 A | 4/2000 | Lysson et al. |
| 6,048,352 A | 4/2000 | Douglas et al. |
| D424,696 S | 5/2000 | Ray et al. |
| D426,638 S | 6/2000 | Ray et al. |
| 6,071,294 A | 6/2000 | Simons et al. |
| 6,071,391 A | 6/2000 | Gotoh et al. |
| 6,083,710 A | 7/2000 | Heller et al. |
| 6,103,199 A | 8/2000 | Bjornson et al. |
| 6,107,083 A | 8/2000 | Collins et al. |
| 6,120,676 A | 9/2000 | Heller et al. |
| 6,143,164 A | 11/2000 | Heller et al. |
| 6,241,863 B1 | 6/2001 | Montbouquette |
| 6,299,757 B1 | 10/2001 | Feldman et al. |
| 6,329,161 B1 | 12/2001 | Heller et al. |
| 6,338,790 B1 | 1/2002 | Feldman et al. |
| 6,379,317 B1 | 4/2002 | Kintzig et al. |
| 6,461,496 B1 | 10/2002 | Feldman et al. |
| 6,464,849 B1 | 10/2002 | Say et al. |
| 6,503,381 B1 | 1/2003 | Gotoh et al. |
| 6,560,471 B1 | 5/2003 | Heller et al. |
| 6,561,989 B2 | 5/2003 | Whitson |
| 6,576,101 B1 | 6/2003 | Heller et al. |
| 6,591,125 B1 | 7/2003 | Buse et al. |
| 6,592,745 B1 | 7/2003 | Feldman et al. |
| 6,607,658 B1 | 8/2003 | Heller et al. |
| 6,610,978 B2 | 8/2003 | Yin et al. |
| 6,616,819 B1 | 9/2003 | Liamos et al. |
| 6,618,934 B1 | 9/2003 | Feldman et al. |
| 6,620,112 B2 | 9/2003 | Klitmose |
| 6,676,816 B2 | 1/2004 | Mao et al. |
| 6,706,159 B2 | 3/2004 | Moerman et al. |
| 6,707,554 B1 | 3/2004 | Miltner et al. |
| 6,740,214 B1 | 5/2004 | Dobson et al. |
| 6,749,740 B2 | 6/2004 | Liamos et al. |
| 6,783,502 B2 | 8/2004 | Orloff et al. |
| 6,840,912 B2 | 1/2005 | Kloepfer et al. |
| 6,881,551 B2 | 4/2005 | Heller et al. |
| 6,893,545 B2 | 5/2005 | Gotoh et al. |
| 6,965,791 B1 | 11/2005 | Hitchcock et al. |
| 7,008,799 B1 | 3/2006 | Zimmer et al. |
| 7,058,437 B2 | 6/2006 | Buse et al. |
| 7,211,437 B2 | 5/2007 | Schabbach et al. |
| 7,264,139 B2 | 9/2007 | Brickwood et al. |
| 7,282,705 B2 | 10/2007 | Brennen |
| 7,299,081 B2 | 11/2007 | Mace et al. |
| 7,322,942 B2 | 1/2008 | Roe |
| 7,335,294 B2 | 2/2008 | Heller et al. |
| 7,344,499 B1 | 3/2008 | Prausnitz et al. |
| 7,378,007 B2 | 5/2008 | Moerman et al. |
| 7,396,334 B2 | 7/2008 | Kuhr et al. |
| 7,585,278 B2 | 9/2009 | Aceti et al. |
| 7,723,099 B2 | 5/2010 | Miller et al. |
| 7,740,581 B2 | 6/2010 | Buse et al. |
| 7,828,749 B2 | 11/2010 | Douglas et al. |
| 7,829,023 B2 | 11/2010 | Burke et al. |
| 7,860,544 B2 | 12/2010 | Say et al. |
| 2002/0040208 A1 | 4/2002 | Flaherty et al. |
| 2002/0098124 A1 | 7/2002 | Bentsen et al. |
| 2004/0087033 A1 | 5/2004 | Schembri |
| 2004/0102717 A1 | 5/2004 | Qi |

(56) References Cited

U.S. PATENT DOCUMENTS

| | | | |
|---|---|---|---|
| 2004/0236251 A1* | 11/2004 | Roe et al. | 600/583 |
| 2005/0067737 A1 | 3/2005 | Rappin et al. | |
| 2005/0089944 A1 | 4/2005 | Shieh et al. | |
| 2005/0196747 A1 | 9/2005 | Stiene | |
| 2005/0197548 A1 | 9/2005 | Dietiker | |
| 2005/0277850 A1* | 12/2005 | Mace et al. | 600/584 |
| 2006/0219576 A1* | 10/2006 | Jina | 205/792 |
| 2006/0241517 A1 | 10/2006 | Fowler et al. | |
| 2007/0100222 A1* | 5/2007 | Mastrototaro et al. | 600/365 |
| 2007/0149897 A1 | 6/2007 | Ghesquiere et al. | |
| 2007/0191702 A1* | 8/2007 | Yodfat et al. | 600/365 |
| 2007/0191736 A1* | 8/2007 | Alden | 600/583 |
| 2008/0017645 A1 | 1/2008 | Garagiola | |
| 2008/0045925 A1* | 2/2008 | Stepovich et al. | 604/518 |
| 2008/0097546 A1 | 4/2008 | Powers et al. | |
| 2008/0167578 A1 | 7/2008 | Bryer et al. | |
| 2009/0021901 A1 | 1/2009 | Stothers | |
| 2009/0032760 A1 | 2/2009 | Muscatell | |
| 2009/0069654 A1 | 3/2009 | Yasuzawa et al. | |
| 2009/0178923 A1 | 7/2009 | Marquant et al. | |
| 2009/0257917 A1 | 10/2009 | Nakamura et al. | |
| 2010/0018869 A1 | 1/2010 | Feldman et al. | |
| 2010/0018871 A1 | 1/2010 | Feldman et al. | |
| 2010/0051479 A1 | 3/2010 | Heller et al. | |
| 2010/0059372 A1 | 3/2010 | Heller et al. | |
| 2010/0059373 A1 | 3/2010 | Heller et al. | |
| 2010/0072063 A1 | 3/2010 | Heller et al. | |
| 2010/0072064 A1 | 3/2010 | Heller et al. | |
| 2010/0326842 A1 | 12/2010 | Mazza et al. | |
| 2011/0028815 A1 | 2/2011 | Simpson et al. | |
| 2011/0086373 A1 | 4/2011 | Wallace-Davis et al. | |
| 2011/0189762 A1 | 8/2011 | Say | |
| 2011/0203941 A1 | 8/2011 | Say | |
| 2011/0265944 A1 | 11/2011 | Say | |
| 2011/0266149 A1 | 11/2011 | Say | |
| 2012/0291254 A1 | 11/2012 | Say | |

FOREIGN PATENT DOCUMENTS

| | | | |
|---|---|---|---|
| EP | 0 256 415 A2 | 2/1988 | |
| EP | 0 327 658 A1 | 8/1989 | |
| EP | 0 409 033 A2 | 1/1991 | |
| EP | 0 420 296 A1 | 4/1991 | |
| EP | 0 592 805 A2 | 4/1994 | |
| EP | 0 710 835 A2 | 5/1996 | |
| EP | 0 792 620 A2 | 9/1997 | |
| EP | 0 965 301 A1 | 12/1999 | |
| EP | 1 462 775 B1 | 12/2007 | |
| JP | 64-3552 | 1/1989 | |
| JP | 1-153952 | 6/1989 | |
| JP | 1-263537 | 10/1989 | |
| JP | 4-279854 | 10/1992 | |
| JP | 6-174946 | 6/1994 | |
| JP | 8-107890 | 4/1996 | |
| JP | 2007-202632 | 8/2007 | |
| JP | 2007-202632 A * | 8/2007 | A61B 5/14 |
| WO | WO 89/07139 | 8/1989 | |
| WO | WO 91/15993 | 10/1991 | |
| WO | WO 94/10553 | 5/1994 | |
| WO | WO 96/22730 | 8/1996 | |
| WO | WO 96/39616 | 12/1996 | |
| WO | WO 97/15827 | 5/1997 | |
| WO | WO 00/35340 | 6/2000 | |
| WO | WO 2005/051183 A1 | 6/2005 | |
| WO | WO 2007/091633 A1 | 8/2007 | |
| WO | WO 2008/017645 A1 | 2/2008 | |
| WO | WO 2009/032760 A2 | 3/2009 | |
| WO | WO 2009/051901 A2 | 4/2009 | |
| WO | WO 2010/056869 A2 | 5/2010 | |
| WO | WO 2010/056876 A2 | 5/2010 | |
| WO | WO 2010/056878 A2 | 5/2010 | |

OTHER PUBLICATIONS

Gough, D. et al., "Short-term In Vivo operation of a glucose sensor," *A.S.A.I.O. Transactions*, vol. 32, No. 1, pp. 148-150 (Jul.-Sep. 1986).

International Search Report and Written Opinion for PCT/US2008/074649 mailed Apr. 20, 2009.

International Search Report and Written Opinion for PCT/US2008/074644 mailed May 14, 2009.

International Search Report and Written Opinion for PCT/US2009/064216 mailed May 3, 2010.

International Search Report and Written Opinion for PCT/US2009/064225 mailed May 4, 2010.

International Search Report and Written Opinion for PCT/US2009/064228 mailed Jul. 1, 2010.

Jaraba, P. et al., "NADH amperometric sensor based on poly(3-methylthiophene)-coated cylindrical carbon fiber microelectrodes: application to the enzymatic determination of L-lactate," *Electrochimica Acta.*, vol. 43, No. 23, pp. 3555-3565 (1998).

Netchiporouk, L.I. et al., "Properties of carbon fibre microelectrodes as a basis for enzyme biosensors," *Analytica Chimica Acta*, vol. 303, pp. 275-283 (1995).

Sakslund, H. et al., "Development and evaluation of glucose microsensors based on electrochemical codeposition of ruthenium and glucose oxidase onto carbon fiber microelectrodes," *Journal of Electroanalytical Chemistry*, vol. 397, pp. 149-155 (1995).

Sakslund, H. et al, "Analysis of the factors determining the sensitivity of a miniaturized glucose biosensor made by codeposition of palladium and glucose oxidase onto an 8 µm carbon filter," *Journal of Electroanalytical Chemistry*, vol. 402, pp. 149-160 (1996).

\* cited by examiner

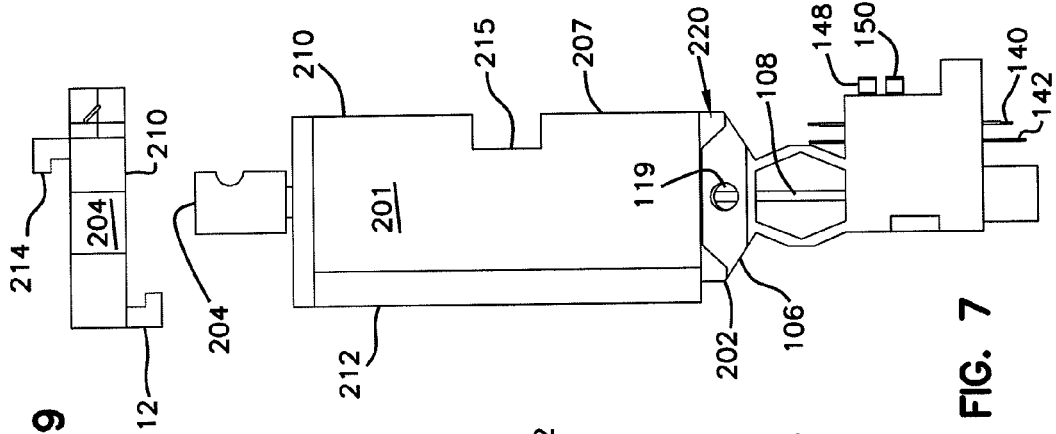
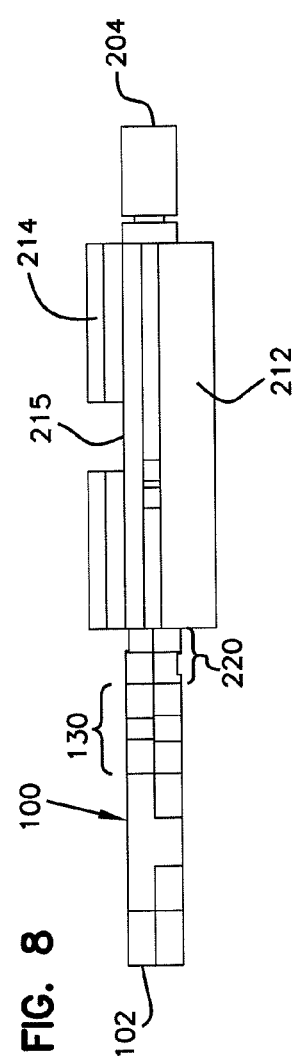
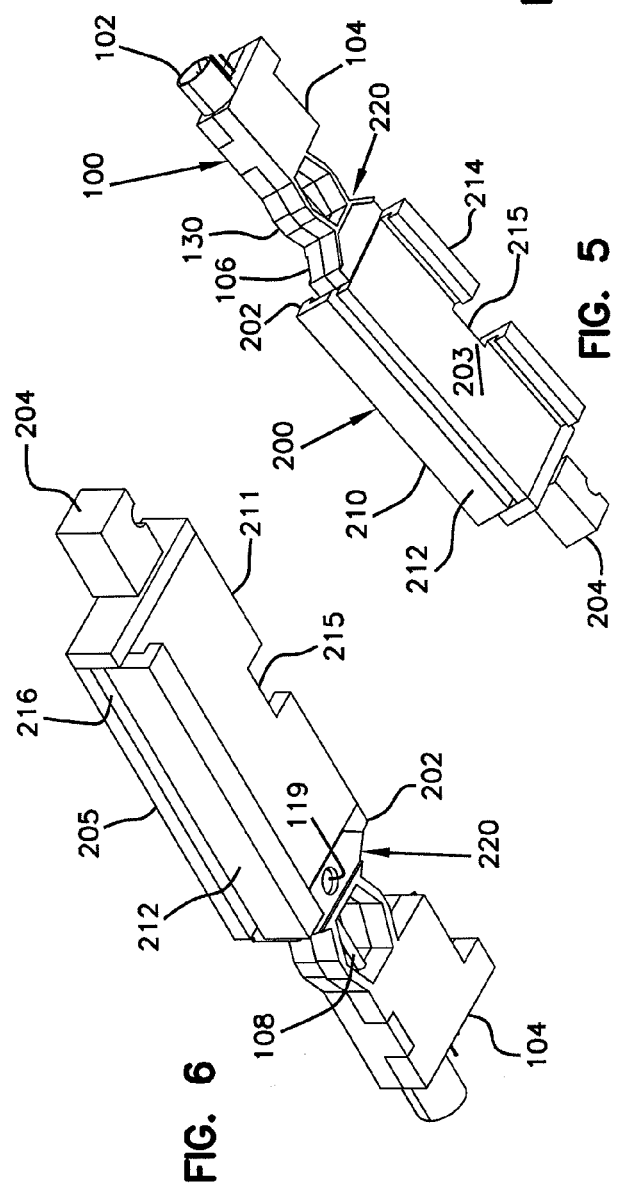

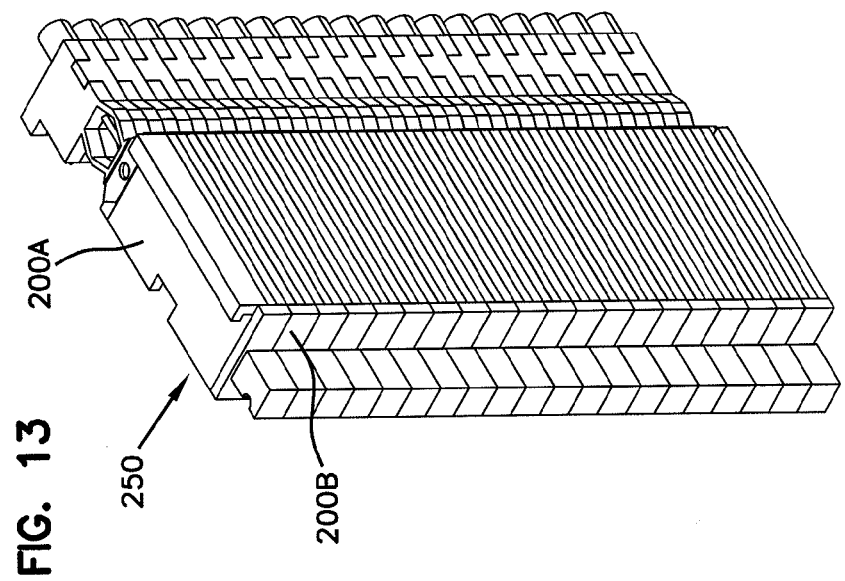
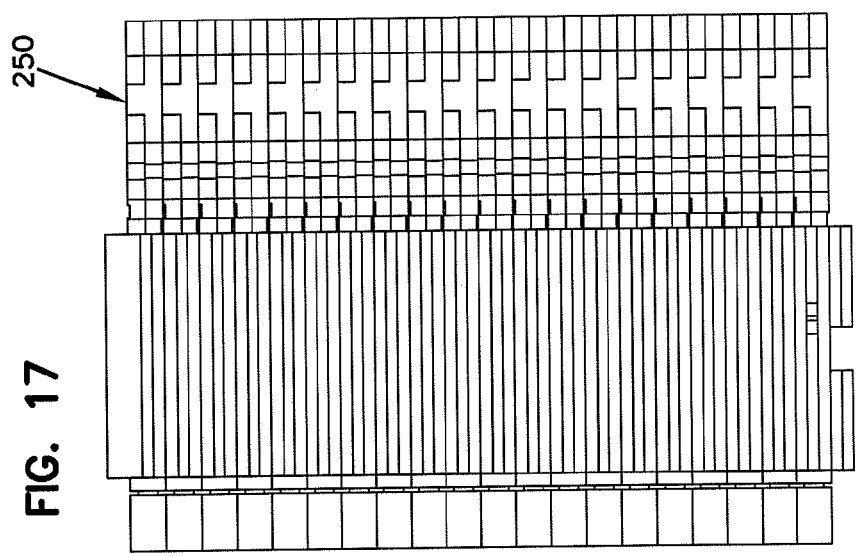

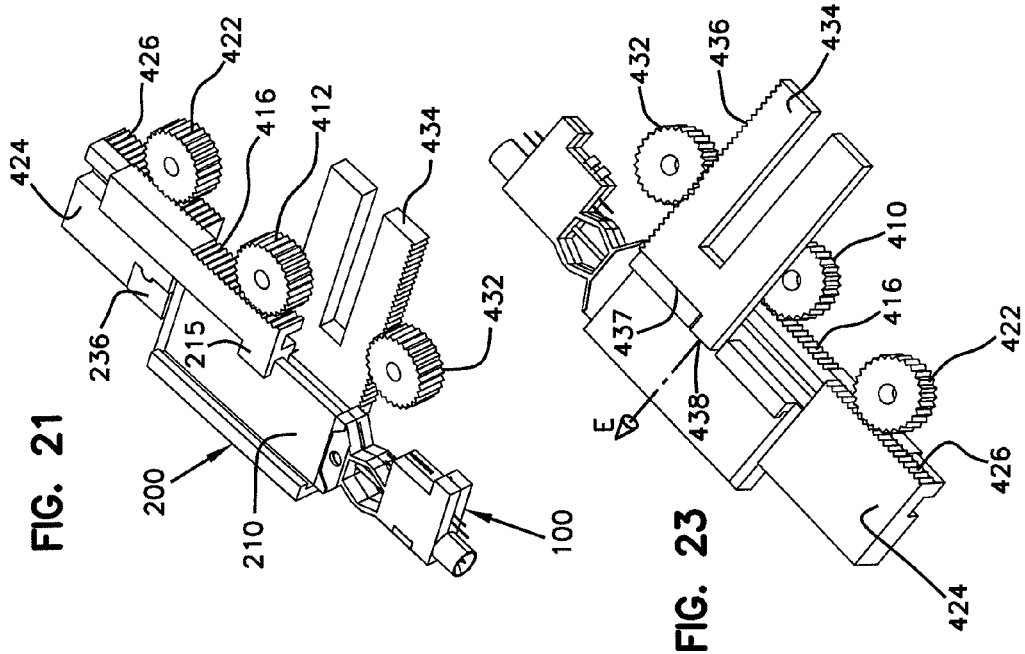
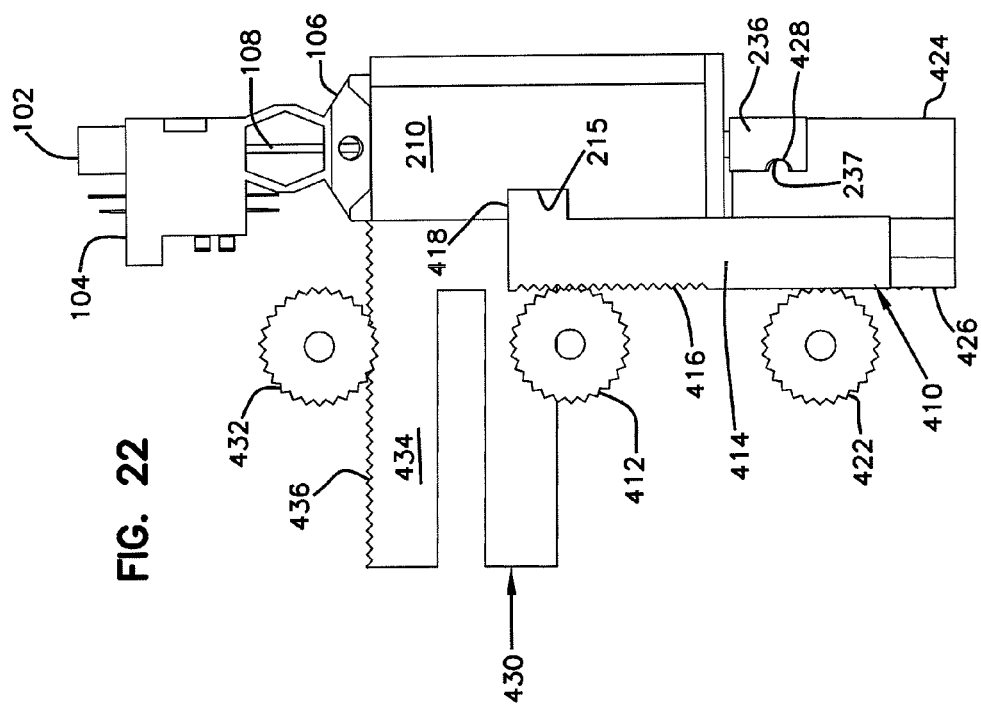

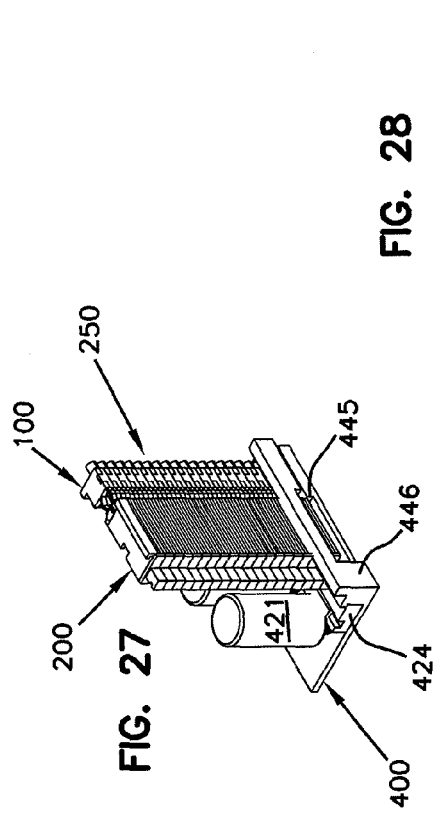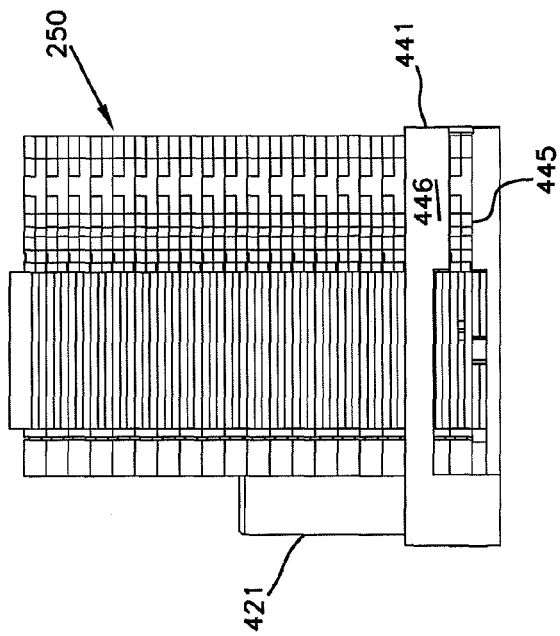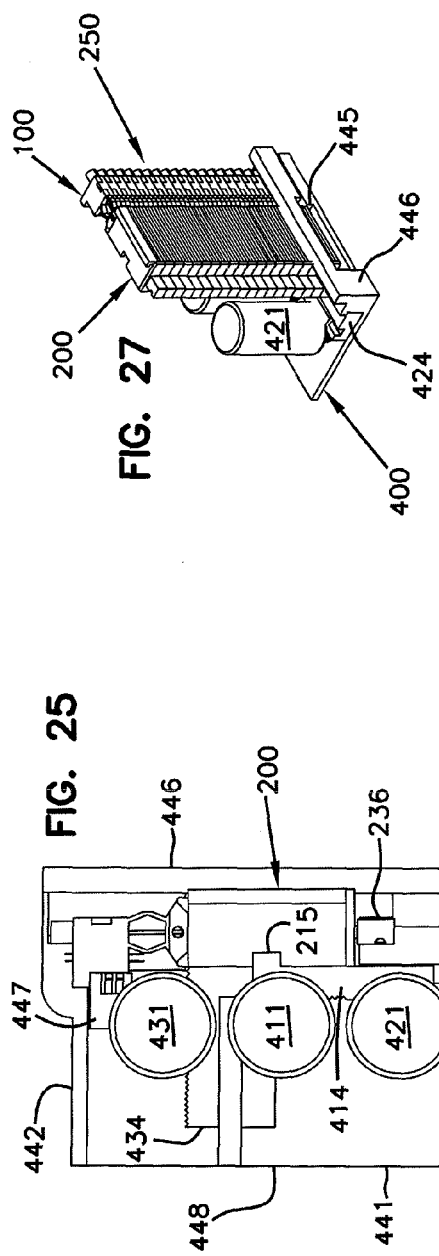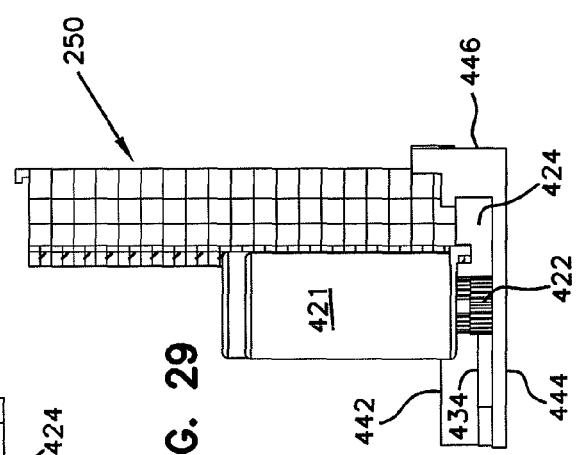

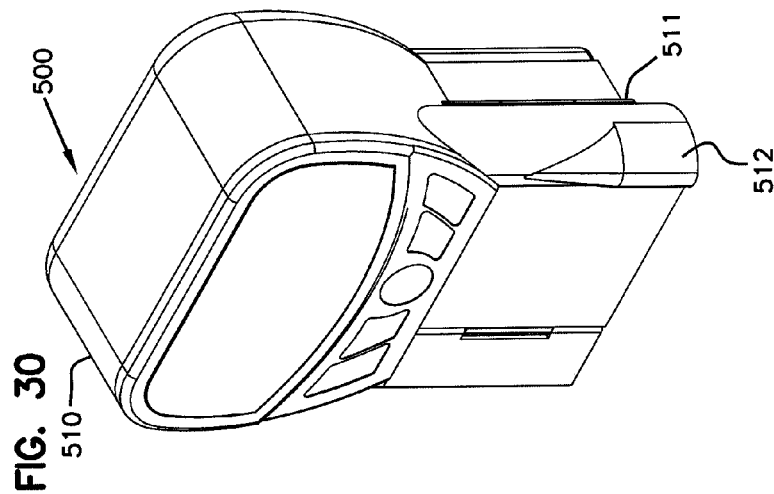
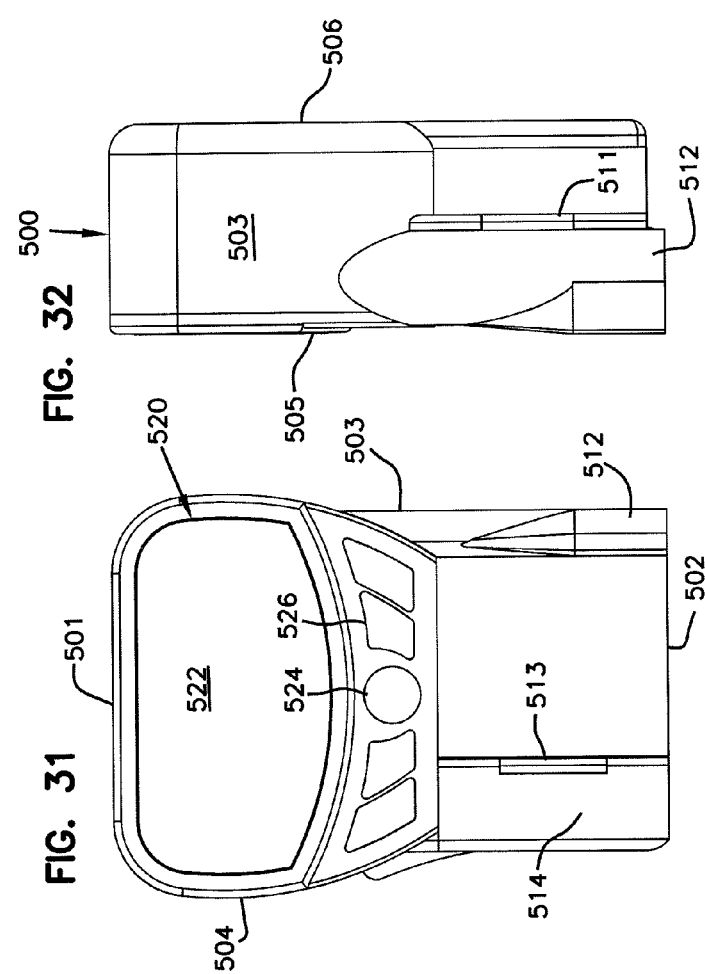

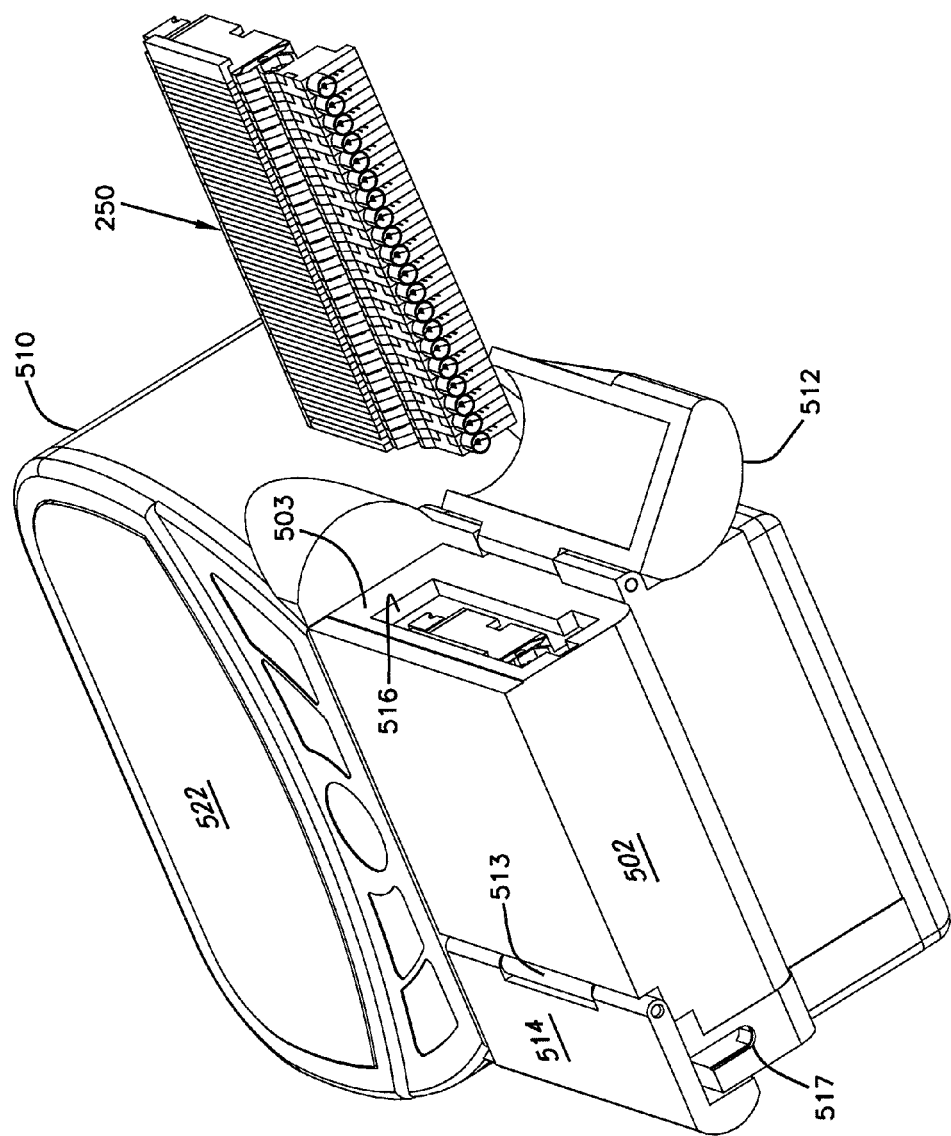

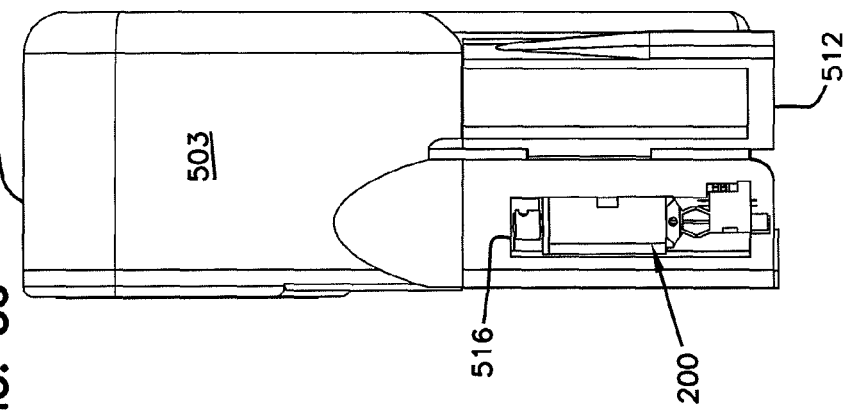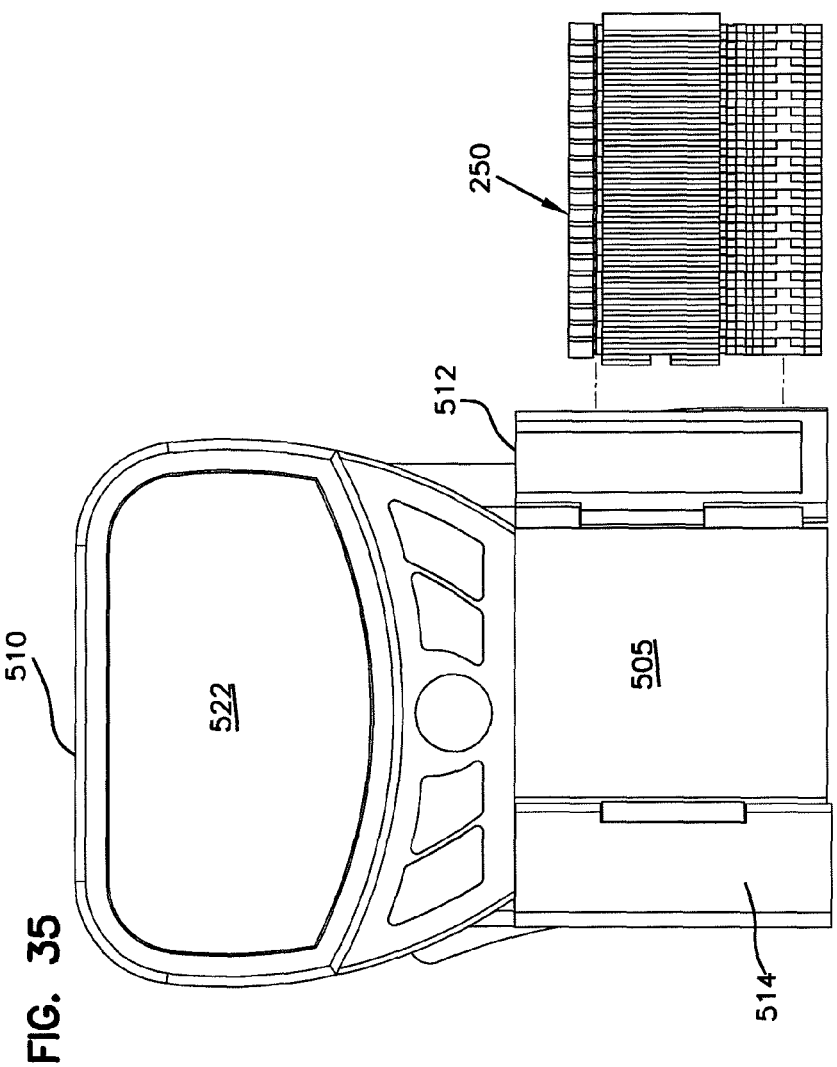

ELECTROCHEMICAL SENSOR MODULE

This application is a National Stage Application of PCT/US2009/064228, filed 12 Nov. 2009, which claims benefit of Ser. No. 61/114,844, filed 14 Nov. 2008 in the USA and which applications are incorporated herein by reference. To the extent appropriate, a claim of priority is made to each of the above disclosed applications.

TECHNICAL FIELD

The present disclosure relates to sensors for measuring one or more bioanalytes and to methods for making such sensors. The present disclosure also relates to systems and methods for delivering therapy based on the measured bioanalyte.

BACKGROUND

Electrochemical bio-sensors have been developed for detecting analyte concentrations in a given fluid sample. For example, U.S. Pat. Nos. 5,264,105; 5,356,786; 5,262,035; 5,320,725; and 6,464,849, which are hereby incorporated herein by reference in their entireties, disclose wired enzyme sensors for detecting analytes, such as lactate or glucose. Wired enzyme sensors have been widely used in blood glucose monitoring systems adapted for home use by diabetics to allow blood glucose levels to be closely monitored. Other example types of blood glucose monitoring systems are disclosed by U.S. Pat. Nos. 5,575,403; 6,379,317; and 6,893,545.

SUMMARY

One aspect of the present disclosure relates to a sensor system that can be manufactured in reduced scale and that can be conveniently handled by consumers.

Another aspect of the present disclosure relates to a sensor module including a molded body that defines an analyte analysis cell and also integrates a skin piercing element, such as a lancet or canula, into the molded body.

A further aspect of the present disclosure relates to an electrochemical sensor module having a configuration that facilitates mounting a plurality of the sensor modules in a module that can easily and conveniently be handled by a consumer.

A further aspect of the present disclosure relates to a glucose monitoring system that integrates a glucose monitor, a skin piercing mechanism, a syringe, an insulin vial, and one or more glucose sensors into a user-friendly glucose monitoring kit.

Still another aspect of the present disclosure relates to an electrochemical sensor module for use in a sensor system that can be efficiently manufactured (e.g., using a continuous manufacturing process such as a continuous insert molding process).

A variety of additional aspects will be set forth in the description that follows. The aspects can relate to individual features and to combinations of features. It is to be understood that both the forgoing general description and the following detailed description are exemplary and explanatory only and are not restrictive of the broad concepts upon which the embodiments disclosed herein are based.

BRIEF DESCRIPTION OF THE DRAWINGS

FIG. 5 is a bottom, isometric view of a cartridge element including the sensor module of FIG. 1 coupled to a delivery arrangement in accordance with the principles of the present disclosure;

FIG. 6 is a top, isometric view of the cartridge element of FIG. 5 in accordance with the principles of the present disclosure;

FIG. 7 is a plan view of the cartridge element of FIG. 5 in accordance with the principles of the present disclosure;

FIG. 8 is a side view of the cartridge element of FIG. 5 from the second side in accordance with the principles of the present disclosure;

FIG. 9 is an end view of the cartridge element of FIG. 5 in accordance with the principles of the present disclosure;

FIG. 13 is a top, isometric view of multiple cartridge elements stacked into a cartridge assembly in accordance with the principles of the present disclosure;

FIG. 17 is a side view of the cartridge assembly of FIG. 13 in accordance with the principles of the present disclosure;

FIG. 21 is a top, isometric view of first, second, and third drive mechanisms interacting with the cartridge element of FIG. 13 in accordance with the principles of the present disclosure;

FIG. 22 is a plan view of the first, second, and third drive mechanisms and the cartridge element of FIG. 21 in accordance with the principles of the present disclosure;

FIG. 23 is a bottom, isometric view of the first, second, and third drive mechanisms and the cartridge element of FIG. 21 in accordance with the principles of the present disclosure;

FIG. 25 is a plan view of the drive system and base of FIG. 24 in accordance with the principles of the present disclosure;

FIG. 27 is a top, isometric view of a cartridge assembly mounted on the drive system of FIG. 24 in accordance with the principles of the present disclosure;

FIG. 28 is a side view of the cartridge assembly and drive system of FIG. 27 in accordance with the principles of the present disclosure;

FIG. 29 is a proximal end view of the cartridge assembly and drive system of FIG. 27 in accordance with the principles of the present disclosure;

FIG. 30 is a front, top isometric view of a monitoring and delivery device in accordance with the principles of the present disclosure;

FIG. 31 is a front view of the monitoring and delivery device of FIG. 30 in accordance with the principles of the present disclosure;

FIG. 32 is a side view of the monitoring and delivery device of FIG. 30 in accordance with the principles of the present disclosure;

FIG. 34 is a bottom, isometric view of the cartridge assembly being loaded into the monitoring and delivery device of FIG. 33 in accordance with the principles of the present disclosure;

FIG. 35 is a front view of the cartridge assembly being loaded into the monitoring and delivery device of FIG. 33 in accordance with the principles of the present disclosure;

FIG. 36 is a side view of the monitoring and delivery device of FIG. 33 with the door being open and the first port being visible in accordance with the principles of the present disclosure;

DETAILED DESCRIPTION

Figure 1:
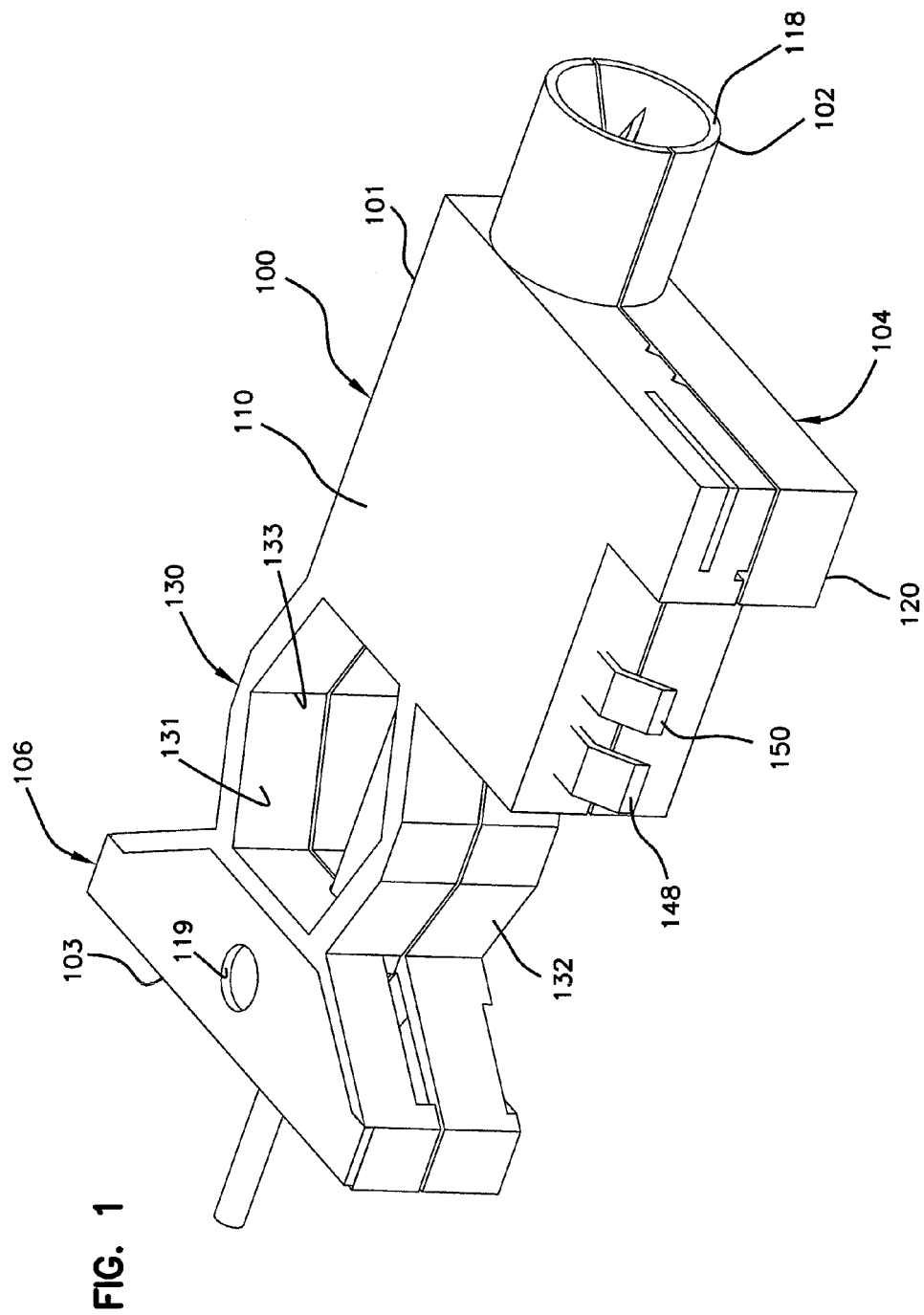
FIG. 1 is an isometric view of a sensor module configured to obtain a fluid sample in accordance with the principles of the present disclosure.

Reference will now be made in detail to exemplary aspects of the present disclosure which are illustrated in the accompanying drawings. Wherever possible, the same reference numbers will be used throughout the drawings to refer to the same or like parts.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are converted (e.g., transduced) to an electrical signal that can be correlated to an amount, concentration, or level of an analyte in the sample. Further details about electrochemical sensing systems, working electrodes, counter electrodes and reference electrodes can be found at U.S. Pat. No. 6,560,471, the disclosure of which is hereby incorporated herein by reference in its entirety.

"Electrolysis" is the electrooxidation or electroreduction of a compound either directly at an electrode or via one or more electron transfer agents.

An "electron transfer agent" is a compound that carries electrons between the analyte and the working electrode either directly or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both.

FIGS. 1-4 illustrate a sensor module 100 configured in accordance with the principles of the present disclosure. The sensor module 100 includes a module body 101 having a distal end 102 positioned opposite from a proximal end 103. The module body 101 is preferably constructed of a molded plastic material. For example, in one embodiment, the module body 101 includes a first molded piece 110 secured to a second molded piece 120 at a part line 105. In one embodiment, the parts 110, 120 are molded using a manufacturing process such as a continuous insert micro-molding process. Details regarding one example of such a manufacturing process can be found in copending application No. 61/114,856, filed Nov. 14, 2008, the disclosure of which is hereby incorporated by reference herein.

The module body 101 includes an analysis cell housing 104 positioned adjacent the distal end 102 and a skin piercing member anchor 106 positioned adjacent the proximal end 103. A flexible linkage 130 mechanically connects the analysis cell housing 104 to the skin piercing member anchor 106. The flexible linkage 130 is configured to allow the analysis cell housing 104 and the skin piercing member anchor 106 to move relative to one another along an axis A that extends through the module body 101 from the proximal end 103 to the distal end 102. The analysis cell housing 104 defines an analysis cell 112 (FIGS. 2-4) at which a fluid sample (e.g., a blood sample) can be analyzed using a sensor structure, such as a wired enzyme sensor arrangement, in fluid communication with the analysis cell 112.

Figure 2:
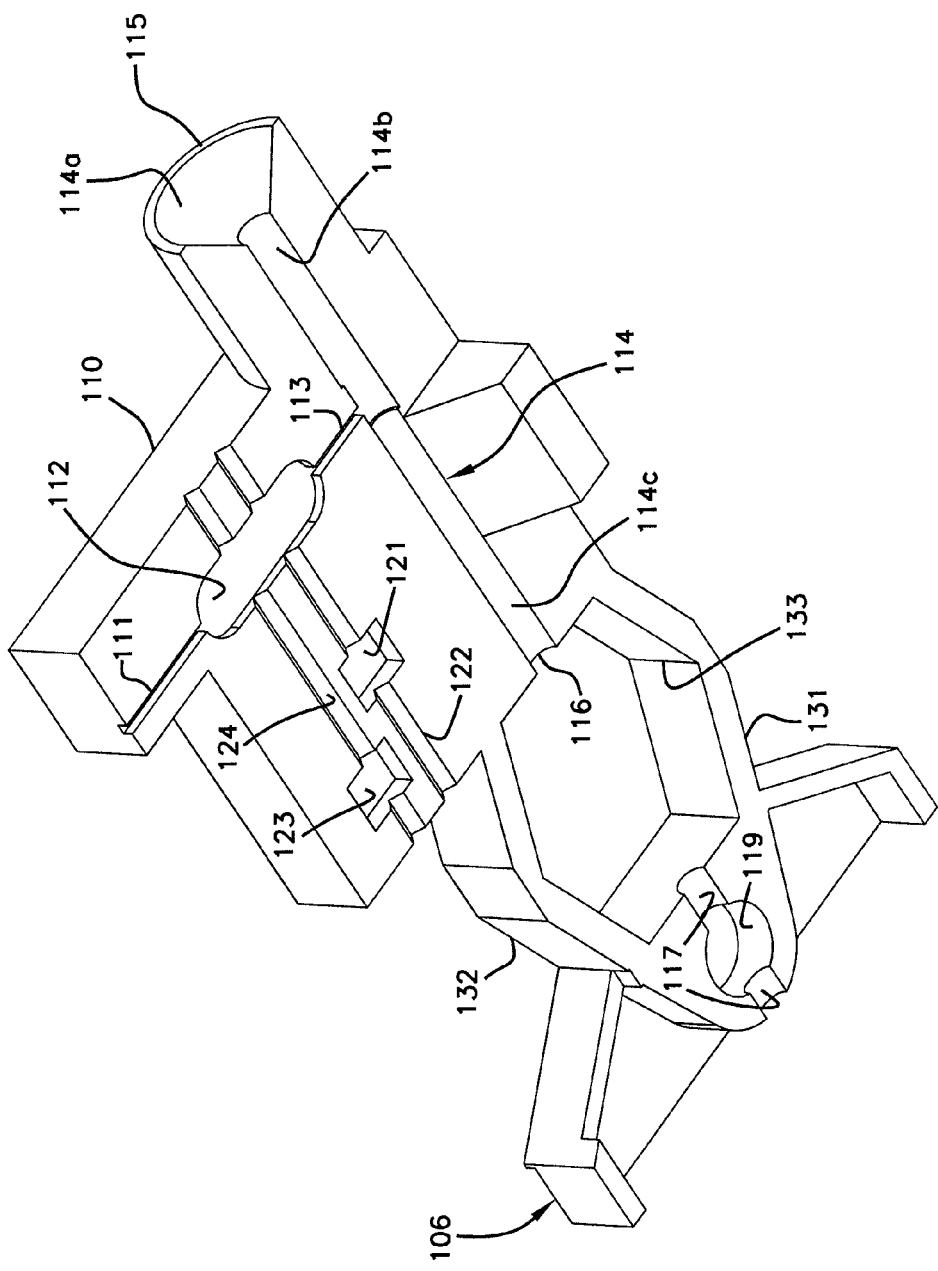
FIG. 2 is an isometric view of a first housing portion of the sensor module of FIG. 1 shown in cross-section so that interior structures of the sensor module are visible, the first housing portion being configured in accordance with the principles of the present disclosure.
Figure 3:
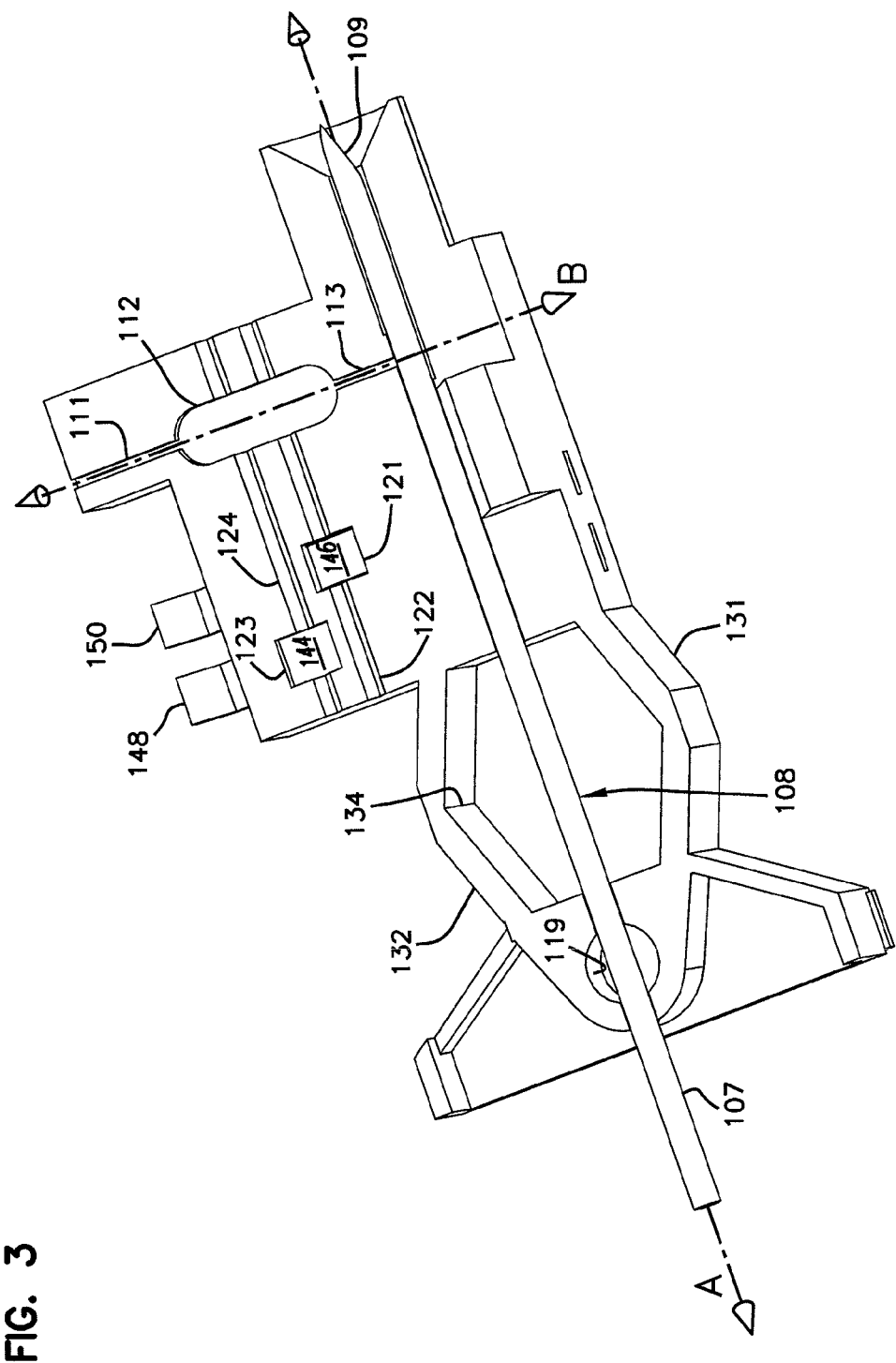
FIG. 3 is another isometric view of the first housing portion of FIG. 2 with a skin piercing member being slideably mounted on the first housing portion in accordance with the principles of the present disclosure.

The sensor module 100 also includes a skin piercing member 108 (e.g., a cannula, a needle, a lancet, or other structure) aligned along the axis A (see FIG. 3). The skin piercing member 108 includes a base end 107 positioned opposite from a piercing tip 109. The base end 107 of the skin piercing member 108 is secured to the skin piercing member anchor 106 and the skin piercing member 109 extends distally from the skin piercing member anchor 106 through a passage 114 defined by the analysis cell housing 104. The passage 114 includes a distal end 115 positioned opposite from a proximal end 116. The passage 114 includes a capillary slot 113 (FIGS. 2 and 3) that provides fluid communication between the analysis cell 112 and the passage 114.

In use of the sensor module 100, the distal end 102 of the module body 101 is placed against a patient's skin at a sampling location where it is desired to take a fluid (e.g., blood) sample. The distal end 102 is configured to stabilize an interface between the module body 101 and the patient's skin when a fluid sample is being taken. The distal end 102 includes a circular, skin engaging surface 118 concentrically aligned with respect to the axis A. When a fluid sample is being taken, the skin engaging surface 118 is pressed against the patient's skin at the sampling location to stabilize the module body 101 and to facilitate insertion of the skin piercing member 108 into the patient's tissue. Once the distal end 102 is in contact with the skin, the skin piercing member anchor 106 can be driven distally along the axis A by an actuator (i.e., a driver) that couples to the skin piercing member anchor 106. Further details regarding some suitable drivers will be provided herein with respect to FIGS. 21-29.

As the skin piercing member anchor 106 is driven distally, the skin piercing member 108 slides within the passage 114 from a retracted position (see FIG. 3) to an extended position (not shown) at which the tip 109 of the skin piercing member 108 extends distally beyond the distal end 102 of the module body 101. The distance the tip 109 of the skin piercing member 108 extends beyond the distal end 102 of the module body 101 is preferably selected to ensure that a blood sample will be drawn efficiently. The skin piercing member anchor 106 is then pulled back proximally by the actuator causing the tip 109 of the skin piercing member 108 to be retracted back into the passage 114.

Penetration by the skin piercing member 108 into the patient's tissue at a wound site causes a blood sample from the wound site to enter the passage 114 and flow by capillary action through the capillary slot 113 to the analysis cell 112. At the analysis cell 112, an analyte level (e.g., the blood glucose level) in the blood sample is sensed by the wired enzyme sensor arrangement that is typically coupled (e.g., wired) to a controller, such as a microcontroller, a mechanical controller, a software driven controller, a hardware driven controller, a firmware driven controller, etc. The controller can include a microprocessor that interfaces with memory. The controller would typically be integrated into an analyte monitor, such as a glucose monitor, having user interfaces for receiving user input (e.g., buttons and switches) and/or providing user output (e.g., a display for displaying the sensed analyte reading). Additional details regarding an example controller suitable for use with the sensor module 100 are provided herein with respect to FIGS. 21-29.

The flexible linkage 130 of the module body 101 preferably has a compressible configuration that enables the flexible linkage 130 to compress axially along axis A as the skin piercing member anchor 106 moves the skin piercing member 108 from the retracted position to the extended position. As shown in FIGS. 1-4, one example flexible linkage 130 includes two linkage members 131, 132. Each linkage member 131, 132 has a first end integrally formed with the skin piercing member anchor 106 and a second end integrally formed with the analysis cell housing 104.

Each of the linkage members 131, 132 includes an intermediate flex or hinge point (e.g., a central hinge point) 133, 134, respectively, that enables the linkage member 131, 132 to flex radially outwardly relative to the axis A when the skin piercing member anchor 106 is moved in a distal direction relative to the analysis cell housing 104. The flex or hinge points 133, 134 also enable the linkage members 131, 132 to flex radially inwardly toward the central axis A when the skin piercing member anchor 106 is moved in a proximal direction relative to the analysis cell housing 104. Accordingly, the linkage members 131, 132 expand radially outwardly from the axis A to provide axial shortening of the linkage members 131, 132 along the axis A, and contract radially toward the axis A to allow axial lengthening of the linkage members 131, 132 along the axis A. The flexible linkage 130 also can be referred to as a "dynamic linkage" since it allows for relative movement between the skin piercing member anchor 106 and the analysis cell housing 104.

The passage 114 of the analysis cell housing 104 includes a tapered portion 114a, a sample transport portion 114b, and a skin piercing member guide portion 114c (see FIG. 2). The tapered portion 114a has a taper that narrows as the tapered portion 114a extends in a proximal direction through the analysis cell housing 104. As depicted at FIGS. 2 and 3, the tapered portion 114a of the passage 114 has a truncated, conical shape with a major diameter adjacent the skin engaging surface 102 and a minor diameter adjacent the capillary slot 113. The fluid sample enters the analysis cell housing 104 through the tapered portion 114a of the passage 114.

The sample transport portion 114b extends along the axis A from the tapered portion 114a to the analysis cell 112. The sample transport portion 114b has a larger transverse cross-sectional area than the skin piercing member guide portion 114c. The larger cross-section provided is sized to provide a capillary space along the skin piercing member 108 for allowing the blood sample to travel by capillary action from the tapered portion 114a of the passage 114 to the analysis cell 112. In this way, the transport portion 114b provides a direct path for transporting the fluid sample from the interface of the wound site generated by the skin piercing member 108, up along the outer surface of the skin piercing member 108, through the capillary slot 113, and into the analysis cell 112. Hydrophilic coatings, selective surface treatments, and/or certain moldable polymers can be used to enhance capillary transport along the sample transport portion 114b of the passage 114.

The skin piercing member guide portion 114c of the passage 114 is preferably sized such that it will provide minimum concentric clearance around the skin piercing member 108. In this way, when the skin piercing member 108 is mounted within the passage 114, the skin piercing member guide portion 114c of the passage 114 allows the skin piercing member 108 to slide within the passage 114 while preventing substantial passage of blood or other interstitial fluid proximally beyond the sample transport portion 114b of the passage 114.

As indicated above, the skin piercing member 108 is secured to the skin piercing member anchor 106. For example, the base end 107 of the skin piercing member 108 can be press-fit, adhesively bonded, or otherwise secured within a groove 117 (FIG. 2) defined by the skin piercing member anchor 106 at a location along the axis A. In one embodiment, the groove 117 extends across an opening 119. While the opening 119 is shown as a through-hole, it will be appreciate that the opening 119 could also be a blind hole. Other connection techniques, such as fasteners, snap-fit connections, or other securement arrangements, also could be used to secure the skin piercing member 108 to the piercing member anchor 106.

The analysis cell 112 defined by the analysis cell housing 104 is elongated in a direction that is generally perpendicular relative to the axis A of the passage 114. The analysis cell 112 has a first end in fluid communication with the capillary slot 113 leading to the sample transport portion 114b of the passage 114 and an opposite, second end at which a vent 111 is defined. The length of the analysis cell 112 is aligned along an axis B (see FIG. 3) that is perpendicular relative to the axis A defined by the passage 114.

Figure 4:
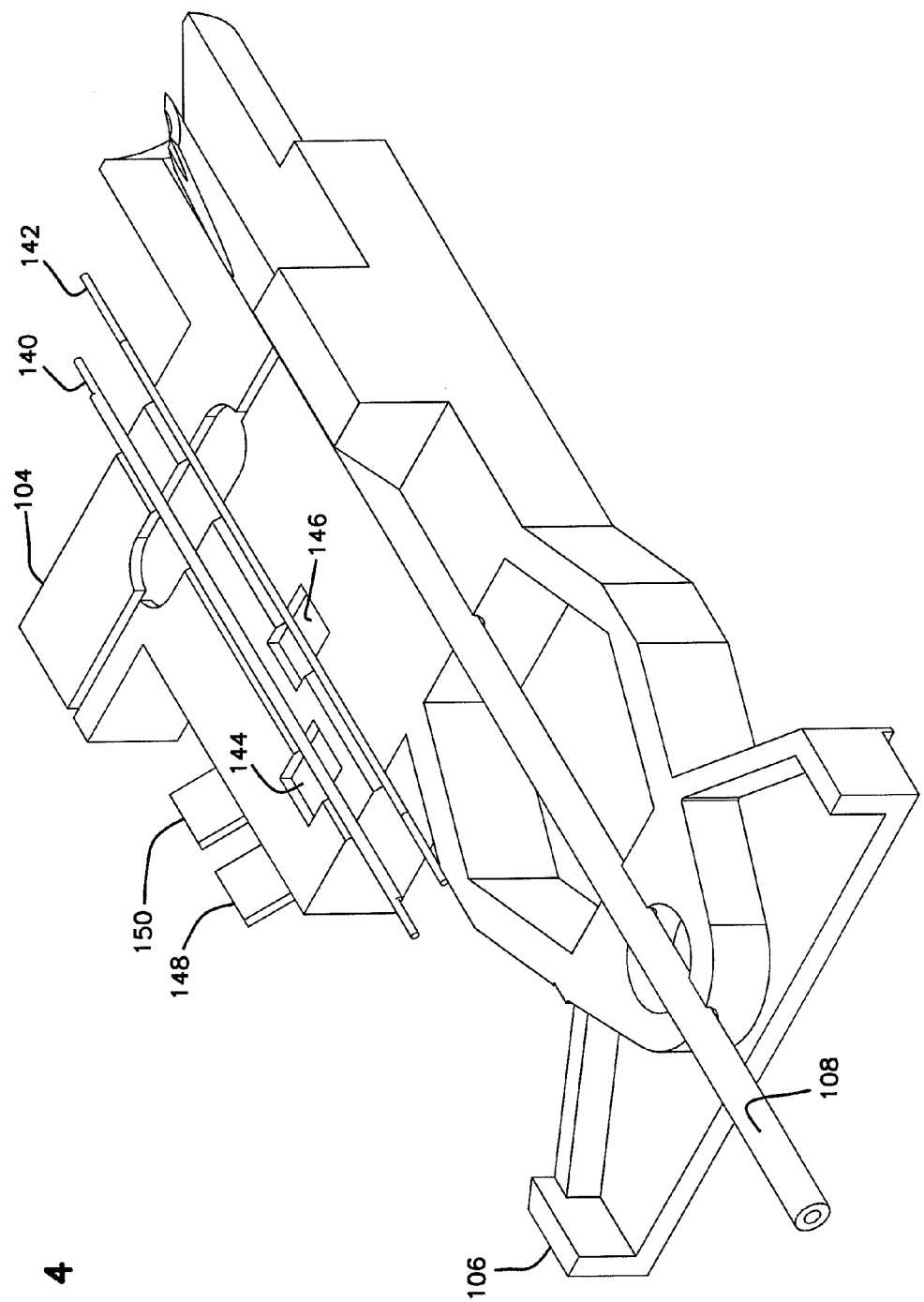
FIG. 4 is another isometric view of the first housing portion of FIG. 3 with first and second electrodes being arranged on the first housing portion in accordance with the principles of the present disclosure.

First and second electrodes 140, 142 extend across the analysis cell 112 in a direction generally perpendicular to the axis B of the analysis cell 112 (see FIG. 4). At least the first electrode 140 generates a signal (e.g., an electrical signal) indicating an analyte concentration level of the sample fluid contained in the analysis cell 112. The analysis cell housing 104 can include contact receivers (e.g., receptacles, pads, slots, or other structures) 121, 123 for receiving and retaining electrode contacts 144, 146 (see FIG. 2). The electrodes 140, 142 extend over the electrode contacts 144, 146 and are configured to transfer the generated signal to the electrode contacts 144, 146. The electrode contacts 144, 146 include exposed tips 148, 150, respectively, protruding outwardly from the analysis cell housing 104 to enable transmission of the analyte concentration level signal to a processor (e.g., see processor 310 of FIG. 21).

In one embodiment, the first electrode 140 is in contact with a sensing layer and functions as a working electrode and the second electrode 142 can function as a reference/counter electrode. In other embodiments, separate working, reference and counter electrodes can be provided in fluid communication with the analysis cell 112. The electrodes 140, 142 are preferably threads, fibers, wires, or other elongated members. The analysis cell housing 104 can include electrode mounting structures in which the electrodes 140, 142 are secured. For example, in one embodiment, the electrode mounting structures can include grooves 122, 124 (e.g., V-grooves) that extend through the analysis cell housing 104 in a direction generally perpendicular relative to the axis B of the analysis cell 112.

In one embodiment, the working electrode 140 can include an elongated member that is coated or otherwise covered with a sensing layer and the reference/counter electrode 142 can include any elongated member, such as a wire or fiber that is coated or otherwise covered with a layer, such as silver chloride. Preferably, at least a portion of each elongated member is electrically conductive. In certain embodiments, each elongated member can include a metal wire or a glassy carbon fiber. In still other embodiments, each elongated member can each have a composite structure and can include a fiber having a dielectric core surrounded by a conductive layer suitable for forming an electrode.

A preferred composite fiber is sold under the name RESISTAT® by Shakespeare Conductive Fibers LLC. This composite fiber includes a composite nylon, monofilament, conductive thread material made conductive by the suffusion of about a 1 micron layer of carbonized nylon isomer onto a dielectric nylon core material. The RESISTAT® material is comprised of isomers of nylon to create the basic two layer composite thread. However, many other polymers are available for the construction, such as: polyethylene terephthalate, nylon 6, nylon 6,6, cellulose, polypropylene cellulose acetate, polyacrylonitrile and copolymers of polyacrylonitrile for a first component and polymers such as of polyethylene terephthalate, nylon 6, nylon 6,6, cellulose, polypropylene cellulose acetate, polyacrylonitrile and copolymers of polyacrylonitrile as constituents of a second component. Inherently conductive polymers (ICP) such as doped polyanaline or polypyrrole can be incorporated into the conductive layer along with the carbon to complete the formulation. In certain embodiments, the ICP can be used as the electrode surface alone or in conjunction with carbon. The RESISTAT® fiber is availability in diameters of 0.0025 to 0.016 inches, which as suitable for sensor electrodes configured in accordance with the principles of the present disclosure. Example patents disclosing composite fibers suitable for use in practicing sensor modules configured in accordance with the principles of the present disclosure include U.S. Pat. Nos. 3,823,035; 4,255,487; 4,545,835 and 4,704,311, which are hereby incorporated herein by reference in their entireties.

The sensing layers provided at working electrodes of sensor modules configured in accordance with the principles of the present disclosure can include a sensing chemistry, such as a redox compound or mediator. The term redox compound is used herein to mean a compound that can be oxidized or reduced. Example redox compounds include transition metal complexes with organic ligands. Preferred redox compounds/mediators include osmium transition metal complexes with one or more ligands having a nitrogen containing heterocycle such as 2,2'-bipyridine. The sensing material also can include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In sensor systems, such as the one being described, these enzymes catalyze the electrolysis of an analyte by transferring electrons between the analyte and the electrode via the redox compound. Further information regarding sensing chemistry can be found at U.S. Pat. Nos. 5,264,105; 5,356,786; 5,262,035; and 5,320,725, which were previously incorporated by reference in their entireties.

In use of the sensor module 100, a fluid sample (e.g., a blood sample) flows through the tapered portion 114a and the sample transport portion 114b of the passage 114 defined in the housing 104 and fills the analysis cell 112. As the analysis cell 112 fills with the fluid sample, the vent 111 allows air within the analysis cell 112 to be displaced by the fluid sample. Once the analysis cell 112 is filled with the fluid sample, a voltage can be applied between the electrodes 140, 142. When the potential is applied, an electrical current will flow through the fluid sample between the electrodes 140, 142. The current is a result of the oxidation or reduction of an analyte, such as glucose, in the volume of fluid sample located within the analysis cell 112. This electrochemical reaction occurs via the electron transfer agent in the sensing layer and an optional electron transfer catalyst/enzyme in the sensing layer. By measuring the current flow generated at a given potential (e.g., with a controller described herein), the concentration of a given analyte (e.g., glucose) in the fluid sample can be determined. Those skilled in the art will recognize that current measurements can be obtained by a variety of techniques including, among other things, coulometric, potentiometric, perometric, voltometric, and other electrochemical techniques.

Referring to FIGS. 5-9, each sensor module 100 can be coupled to a delivery arrangement 210 to form a cartridge element 200. The delivery arrangement 210 has a body 211 extending from a distal end 202 to a proximal end 204. The delivery arrangement body 211, which has a generally rectangular shape, includes a top 201, a bottom 203, a first side 205, and an opposite, second side 207. The body 211 can be manufactured (e.g., injection molded) separately from the sensor module 100.

The distal end 202 of the delivery arrangement body 211 includes a coupling member 220 that is configured to secure the delivery arrangement 210 to the skin piercing member anchor 106 of the sensor module 100. For example, the coupling member 220 can be laser welded, fixed with epoxy, or otherwise secured to the piercing member anchor 106. In one embodiment, the coupling member 220 is shaped and sized to fit or interlock with the skin piercing member anchor 106. In one embodiment, the opening 119 defined in the piercing member anchor 106 is a port through which an adhesive can be injected to secure the delivery arrangement 210 to the sensor module 100.

Figure 10:
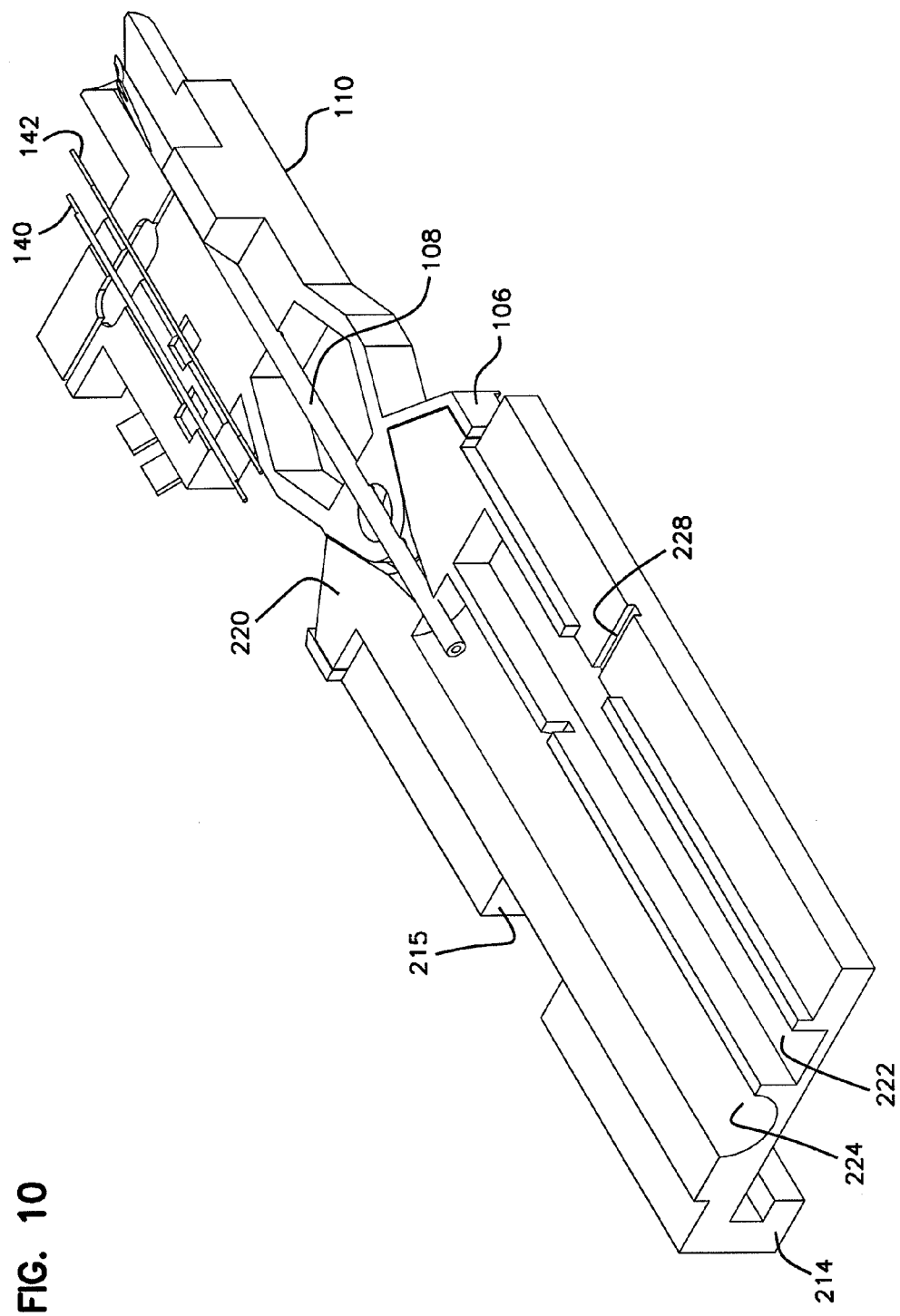
FIG. 10 is an isometric view of the cartridge element of FIG. 5 shown in cross-section such that the skin piercing member, electrodes, and drug reservoir are visible in accordance with the principles of the present disclosure.
Figure 11:
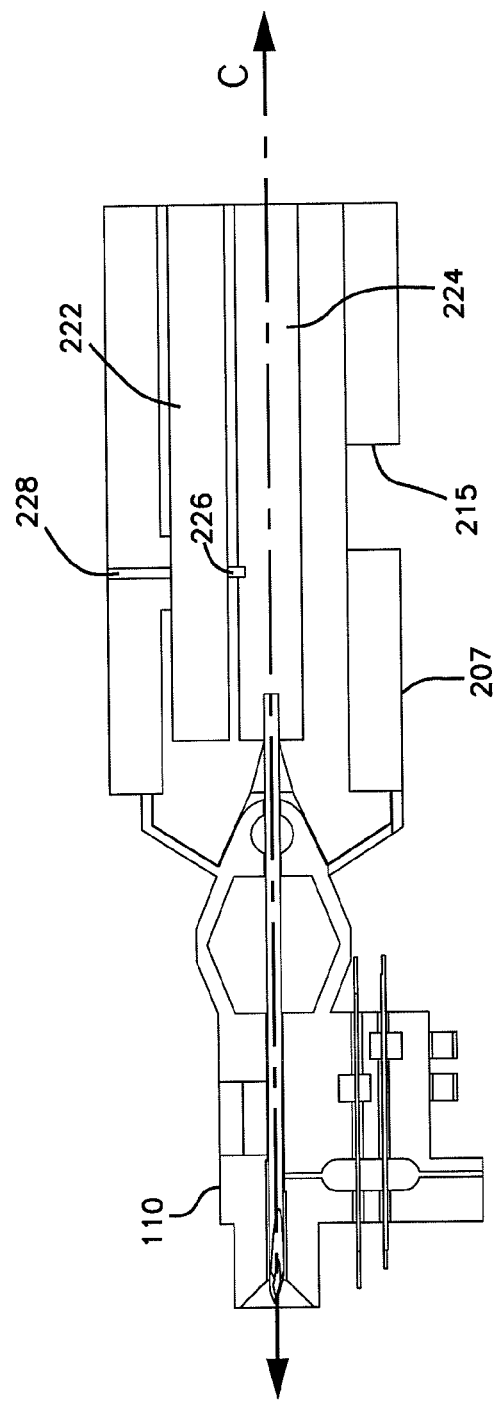
FIG. 11 is a plan, cross-sectional view of the cartridge element of FIG. 10 in accordance with the principles of the present disclosure.
Figure 12:
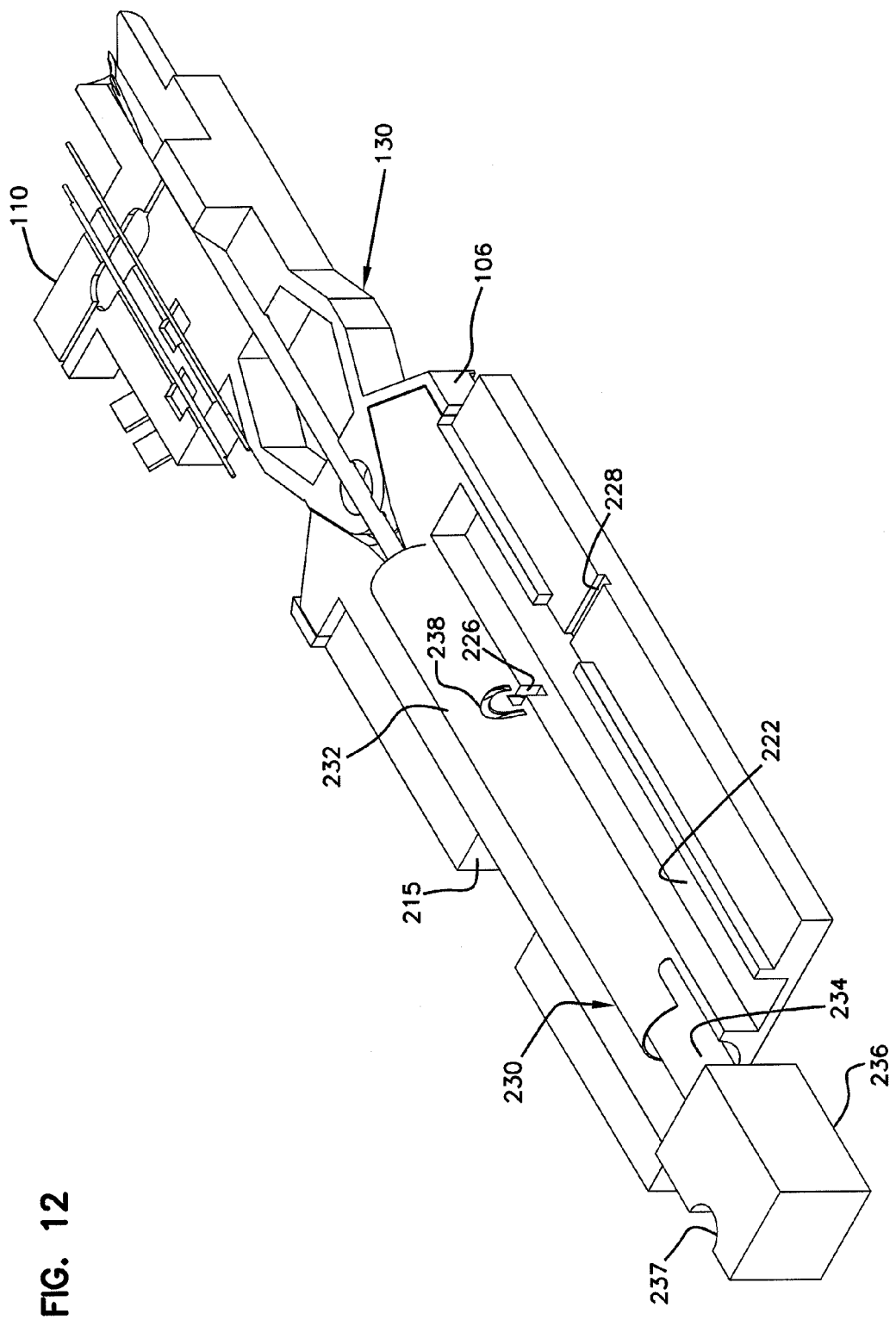
FIG. 12 is an isometric view of the cartridge member of FIG. 10 including a piston chamber mounted to the delivery arrangement in accordance with the principles of the present disclosure.
Figure 18:
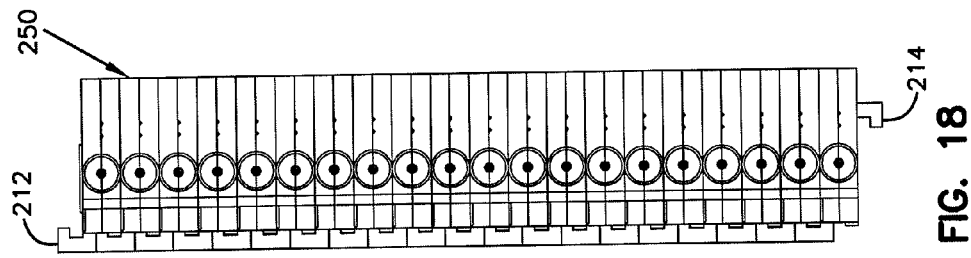
FIG. 18 is a distal end view of the cartridge assembly of FIG. 13 in accordance with the principles of the present disclosure.
Figure 14:
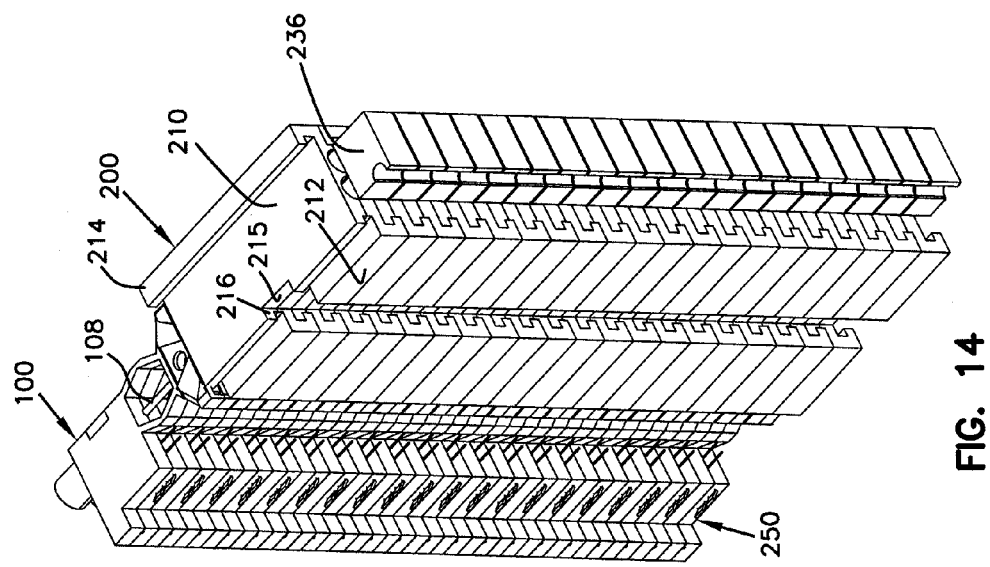
FIG. 14 is another top, isometric view of the cartridge assembly of FIG. 13 in accordance with the principles of the present disclosure.
Figure 19:
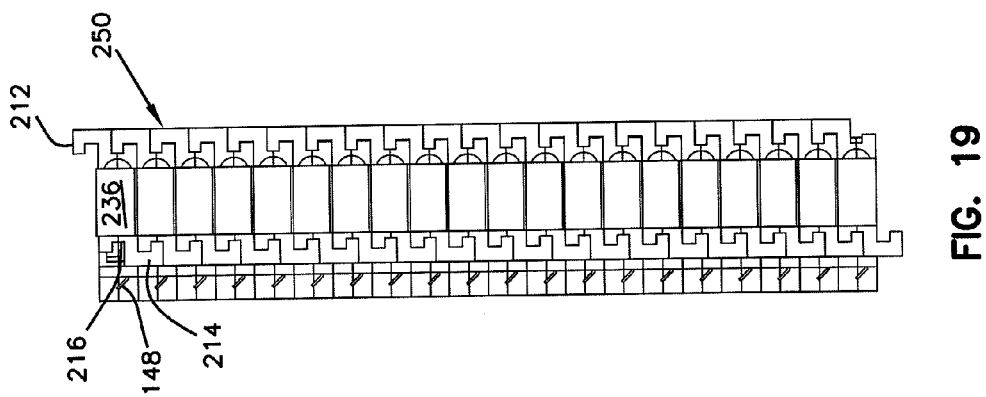
FIG. 19 is a proximal end view of the cartridge assembly of FIG. 13 in accordance with the principles of the present disclosure.
Figure 16:
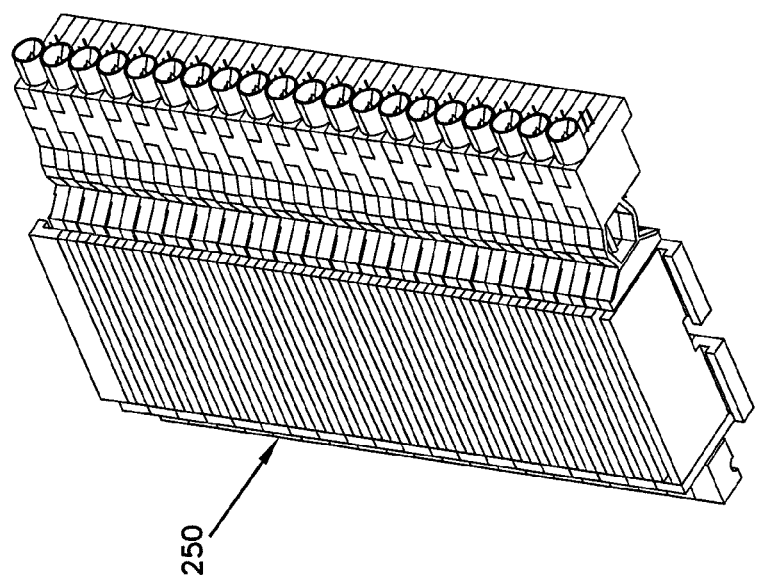
FIG. 16 is another bottom, isometric view of the cartridge assembly of FIG. 13 in accordance with the principles of the present disclosure.
Figure 15:
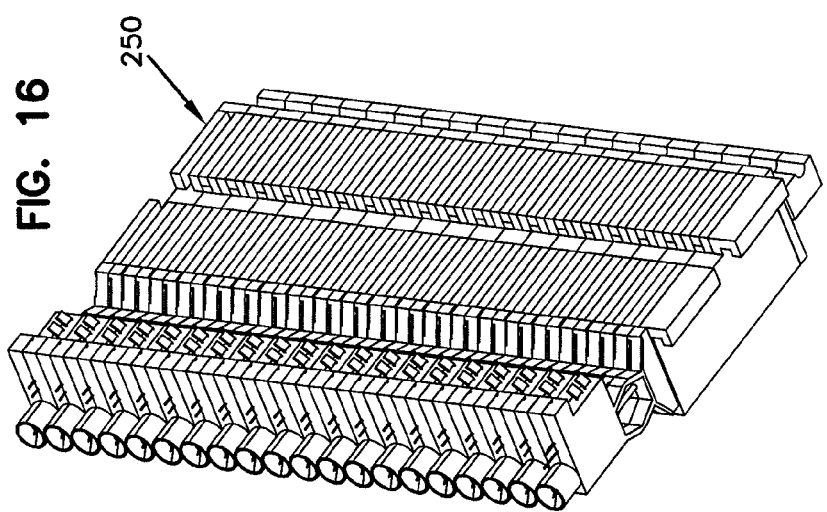
FIG. 15 is a bottom, isometric view of the cartridge assembly of FIG. 13 in accordance with the principles of the present disclosure.

Referring to FIGS. 10-12, the delivery arrangement 210 includes a drug reservoir 222 containing a dosage of a drug (e.g., insulin) to be administered to the patient (e.g., a diabetic patient). In one embodiment, the delivery arrangement 210 can be pre-filled with the drug dosage (e.g., at the factory) prior to coupling the delivery arrangement 210 to the sensor module 100. In other embodiments, the drug dosage can be added to the delivery arrangement 210 after coupling the delivery arrangement 210 to the sensor module 100.

The delivery arrangement 210 also includes a piston chamber 224 extending axially along the body 211 and generally parallel to the drug reservoir 222. The piston chamber 224 is configured to contain a delivery arrangement for dispensing the drug dosage to the patient. The skin piercing member 108 of the sensor module 100 extends proximally from the skin piercing member anchor 106 into the piston chamber 224, thereby providing fluid communication between the piston chamber 224 and the cannula of the skin piercing member 108 at a distal end of the piston chamber 224 (see FIGS. 10 and 11).

An inner wall of the body 211 defines a port 226 that provides fluid communication between the drug reservoir 222 and the piston chamber 224. A vent 228 extends from the drug reservoir 222 to an exterior of the delivery arrangement 210 to enable the drug to flow from the reservoir 222 to the piston chamber 224. The piston chamber 224 includes a valve arrangement 238 configured to enable selective ingress of a drug dosage from the drug reservoir 222 into the piston chamber 224. The valve arrangement 238 inhibits egress of the drug dosage from the piston chamber 224 back into the drug reservoir 222.

In one embodiment, the valve arrangement 238 includes a differential check valve component configured to assist in controlling the flow of the drug dosage from the drug reservoir 222 to the piston chamber 224. In certain embodiments, the valve arrangement 238 is formed on a tube 230 arranged in the piston chamber 224. The tube 230 can be a polymeric tube that lines the piston chamber 230 (see FIG. 12). In one embodiment, the check valve 238 is integrally formed with a thin wall of the tube 230. In the example depicted at FIG. 12, the tube 230 is cut (e.g., laser cut) to form a flat valve 238 that aligns with and seats upon the side port 226 when the tube 230 is mounted within the piston chamber 224.

A piston rod 234 is slideably mounted within the piston chamber 224 such that the piston rod 234 can be moved generally coaxially with the skin piercing member 108 in a proximal or distal direction. A piston head is mounted at a distal end of the piston rod 234 to cooperate with the tube 230 to form a seal. Movement of the piston rod 234 in the proximal direction releases the valve arrangement 238 and enables ingress of the drug dosage into the piston chamber 224. For example, movement of the piston rod 234 in the proximal direction can slide the piston head proximal of the valve arrangement 238, thereby enabling the valve arrangement 238 to flex into the tube 230. Further movement of the piston head in the proximal direction draws the drug from the reservoir 222, through the valve arrangement 238, and into the piston chamber 224. The amount of drug entering the piston chamber 224 depends at least partially on the amount by which the piston rod 234 is proximally drawn. Subsequent movement of the piston rod 234 in the distal direction expels the drug dosage from the piston chamber 224 through the skin piercing member 108.

In general, the cartridge element 200 includes exterior structures configured to allow a plurality of the cartridge elements 200 to be stacked one on top of the other to form a cartridge assembly 250 (see FIGS. 13-19) or magazine that can be loaded into a monitoring and delivery system (e.g., a glucose monitoring and insulin delivery system) 300 (see FIG. 20) as a unit. For example, the delivery arrangement 210 of the cartridge element 200 includes a first and second slots 216 extending along a length of the body 211 between the distal end 202 and proximal end 204. The first slot 216 extends along the first side 205 of the housing 211 and the second slot (not shown) extends along the second side 207 of the housing 211. The slots 216 are generally parallel to an axis C of the cartridge element 200 (see FIG. 11). By generally parallel, it is meant that the slots 216 are parallel or almost parallel to the axis C.

The delivery arrangement 210 also includes first and second rails 212, 214 that are generally parallel to the axis C of the cartridge element 200. The first rail 212 extends from the top 201 of the body 211 along the first side 205 and the second rail 214 extends from the bottom 203 of the body 211 along the second side 207. In one embodiment, each of the rails 212, 214 is generally L-shaped and faces inwardly (see FIG. 9). The rails 212, 214 of each body 211 are configured to protrude into the slots 216 of adjacent delivery arrangements 210 in the cartridge assembly stack 250.

When a first cartridge element 200a is stacked on top of a second cartridge element 200b, the second rail 214 of the cartridge element 200a fits within the first slot 216 of the second cartridge element 200b. The first rail 212 of the second cartridge element 200b fits within the second slot of the first cartridge element 200a. With this slot configuration, the second cartridge element 200b can be connected to the first cartridge element 200a by sliding the second cartridge element 200b relative to the first cartridge element 200a such that slot 216 of the second cartridge element 200b laterally receives the first rail 212 of the first cartridge element 200a and such that a rail 214 of the second cartridge element 200b is laterally received within slot 216 of cartridge element 200a. Cartridge element 200b also can be disconnected from cartridge element 200a by sliding.

Figure 20A:
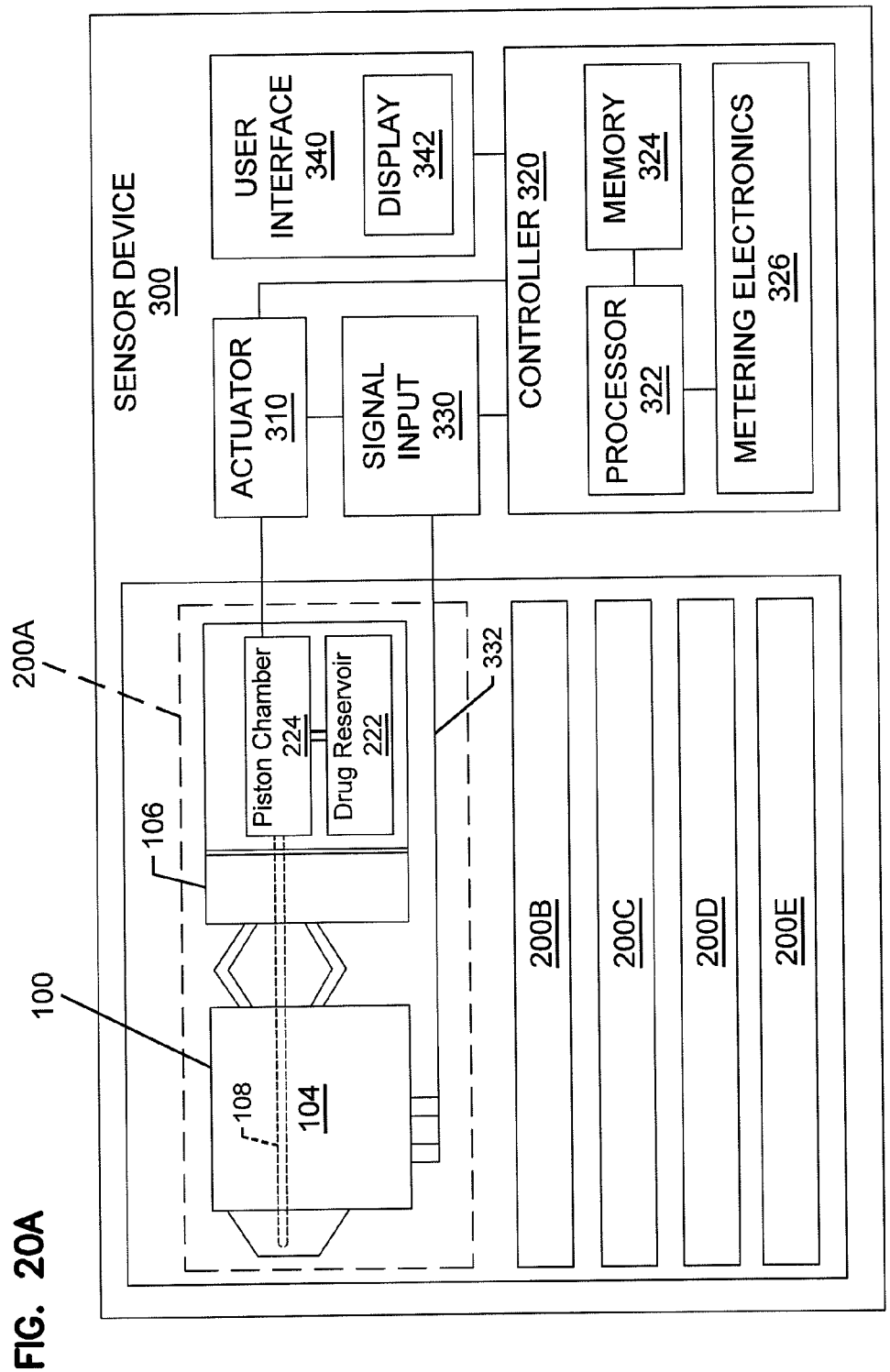
FIG. 20A is a schematic block diagram of a monitoring and delivery system in accordance with the principles of the present disclosure.
Figure 20B:
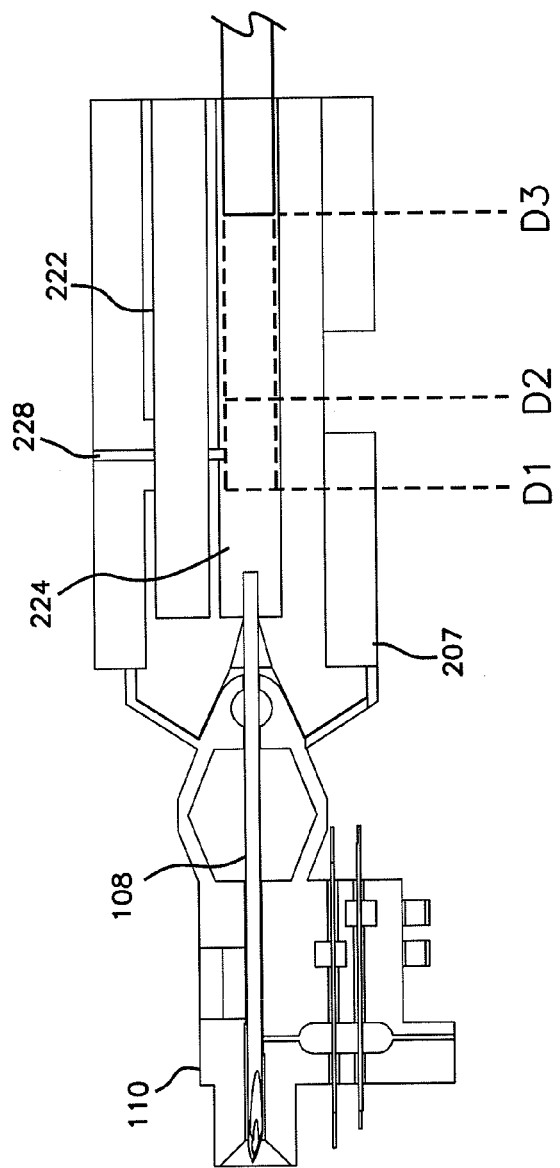
FIG. 20B is a plan view of the cartridge assembly of FIG. 13 shown in cross-section with a piston rod visible in accordance with the principles of the present disclosure.

In general, a cartridge element 200 can be loaded as sub-components into an analyte monitoring and drug delivery system. For example, FIG. 20A is a schematic block diagram of one example monitoring and delivery system 300 configured to determine an analyte level (e.g., glucose level) of a patient and deliver a drug dosage (e.g., insulin) based on the determined analyte level. The cartridge assembly 250 can be loaded into the monitoring and delivery system 300. For example, the monitoring and delivery system 300 shown in FIG. 20A contains five cartridge elements 200A-200E.

The monitoring system 300 includes an actuator 310, a controller 320, a signal input 330, and a user interface 340. The actuator 310 is generally configured to operate the cartridge element 200 (e.g., to obtain a fluid sample from a patient, to dispense a drug dosage, etc.). In some embodiments, the actuator 310 can be mechanically connected to the cartridge element 200 by a rod, piston, or other type of mechanical connector. Alternatively, the actuator 310 can provide movement instructions to the cartridge element 200 via an electrical connection.

In general, the controller 320 includes a processor 322, memory 324, and metering electronics 326. The controller 320 instructs the actuator 310 when to operate the cartridge element 200. For example, the controller 320 can instruct the actuator 310 based on a signal received at the signal input 330. In another embodiment, the controller 320 can instruct the actuator 310 based on instructions received from the user interface 340. The controller 320 also can instruct the actuator 310 to eject a spent cartridge element 200 from the system 300. Typically, each cartridge element 200 is actuated once and then discarded from the system 300. In other uses, however, the cartridge element 200 can be utilized multiple times.

The signal input 330 receives the signal generated at the electrodes 140, 142 of the sensor module 100 of one of the cartridge elements 200 and provides the signal to the controller 320 for analysis. For example, the signal input 330 can obtain the signal via a connection 332 (e.g., a wire, conductive tracing, or other type of electrical conductor) extending between the signal input 330 and the electrode contacts 148, 150. The metering electronics 326 and processor 322 analyze the signal to determine an analyte concentration level (e.g., a blood glucose reading) or other desired information.

The actuator 310 is generally configured to manipulate the cartridge element 200 to obtain a fluid sample by driving the skin piercing members 108 of one of the cartridge elements 200 between the extended and retracted positions. For example, the actuator 310 can be configured to push the respective skin piercing member anchor 106 in a distal direction relative to the analysis cell housing 104 to inject the piercing member 108 into the skin. The actuator 310 also can pull back the piston rod 234 in the piston chamber 224 to draw fluid through the piercing member 108, through the passageway 114, and into the analysis cell 112. Subsequently, the actuator 310 pulls the skin piercing member anchor 106 in a proximal direction relative to the analysis cell housing 104 to withdraw the piercing member 108 from the skin.

The actuator 310 also can be configured to cause the cartridge element 200 to deliver a drug dose. For example, in one embodiment, the actuator 310 can be configured to inject the piercing member 108 at an appropriate depth into the skin of the patient. In another embodiment, the piercing member 108 remains in the skin after obtaining the fluid sample until the drug dosage has been dispensed. The actuator 310 also can be configured to slide the piston rod 234 proximally to fill the piston chamber 224 with a drug dosage from the drug reservoir 222 and to slide the piston rod 234 distally to expel the drug dosage from the piston chamber 224.

In general, the amount of drug drawn from the reservoir 222 into the piston chamber 224 depends on the distance over which the piston rod 234 is proximally drawn. For example, drawing the piston rod 234 from a first position D1, in which the piston rod 234 closes the valve arrangement 238, to a second position D2, in which the piston rod 234 releases the valve arrangement 238, causes a first quantity of drug to enter the piston chamber 224 from the drug reservoir 222 (see FIG. 20B). Drawing the piston rod 234 from the first position D1 to a third position D3, where position D3 is proximal to position D2, causes a second quantity of drug to enter the piston chamber 224 where the second quantity of drug is greater than the first quantity of drug.

The controller 320 determines an appropriate dosage of the drug based on the analysis of the fluid sample and determines the distance over which the piston rod 234 should be drawn to effectuate the dosage. For example, the controller 320 can determine an appropriate dosage of insulin based on a determined blood glucose level of the patient. The correlation between the analyte concentration level and the appropriate drug dose (e.g., one or more tables of values, algorithms, etc.) can be stored in the memory 324. The correlation between the dosage quantity and the distance over which the piston rod 234 is drawn also can be stored in memory 324.

In one embodiment, the controller 320 causes the actuator 310 to draw substantially all of the drug dosage contained in the drug reservoir 222 into the piston chamber 224. In other embodiments, however, the controller 320 causes the actuator 310 to draw only a portion of the drug dosage contained in the drug reservoir 222 into the piston chamber 224. In some embodiments, the controller 320 causes the actuator 310 to draw less than half of the drug dosage into the piston chamber 224. Indeed, in some embodiments, the controller 320 causes the actuator 310 to draw less than a third of the drug dosage into the piston chamber 224. In other embodiments, however, a predetermined amount of drug is dispensed from each cartridge element 200.

In some embodiments, the controller 320 also causes the user interface 340 (e.g., a display screen 342) to indicate the determined analyte concentration level to the user. Other information (e.g., the determined dosage) also can be presented to the user via the user interface 340. In one embodiment, the display 342 is a visual display. In other embodiments, an audio display also can be used. In addition, a user can provide information to the controller 320 via the user interface 340 (e.g., buttons, switches, etc.). For example, the user can initiate operation of the cartridge element 200 by actuating a start interface (e.g., button).

The body 211 of the delivery arrangement 210 can have structures that facilitate mounting the delivery arrangement 210 relative to one or more components of the overall monitoring and delivery system 300. For example, one side of each delivery arrangement 210 can define a slot 215 (see FIGS. 5 and 7) by which the delivery arrangement 210 can be manipulated. In one embodiment, an actuator arm (e.g., arm 412 of FIG. 21) can be inserted into the slot 215 to push and pull the delivery arrangement 210 in a proximal and distal direction. In certain embodiments, a component of the controller 310 can couple to a connector 236 mounted at a proximal end of the piston rod 234. In one embodiment, the connector 236 defines an actuator engagement slot 237 configured to fit with the corresponding component of the controller 310 to enable the controller 310 to selectively move the piston rod 234.

In use, the cartridge element 200 is coupled to a first axial drive mechanism 410 of the monitoring and delivery system 300 and the connector 236 of the piston rod 234 is connected to a second axial drive mechanism 420 of the monitoring and delivery system 300 (see FIGS. 21-24). The axial drive mechanisms 410, 420 are configured to drive the cartridge element 200 and piston rod 234 along the axis C (FIG. 11) of the cartridge element 200. Each of the axial drive mechanisms 410, 420 includes a drive gear 412, 422 and a drive arm 414, 424, respectively. Each drive arm 414, 424 defines a toothed section 416, 426, respectively, which interacts with the respective drive gears 412, 424 to move each arm 414, 424 in the proximal or distal direction.

Figure 26:
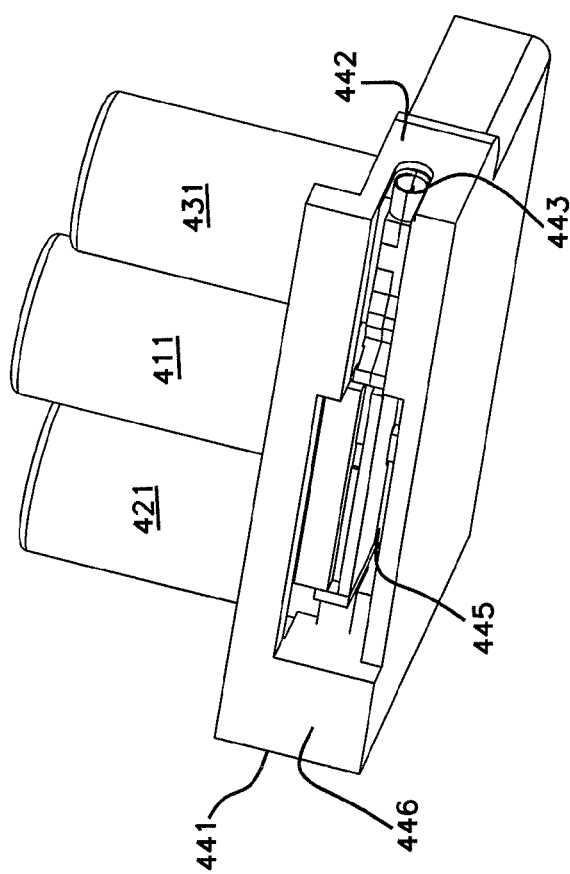
FIG. 26 is a side, isometric view of the drive system of FIG. 24 in accordance with the principles of the present disclosure.

In the example shown in FIGS. 25-26, each drive gear 412, 422, 432 can be powered by a motor 411, 421, 431, respectively. In certain embodiments, the motors 411, 421, 431 can include stepper motors that drive the pinion gears 412, 422 and 432. The motor 411 functions to drive the delivery arrangement 210 of the bottommost cartridge element 200 along the axis C of the cartridge element 200. The pinion gear 412 of the motor 411 drives a gear rack 414 proximally and distally along an axis parallel to or coaxial with the axis C of the cartridge element 200. The gear rack 414 includes a tab 418 that fits within a corresponding notch 215 defined by the body 211 of the delivery arrangement 210 to prevent relative axial movement between the gear rack 414 and the delivery arrangement 210.

Motor 421 functions as a piston actuator for driving the piston rod 234 of the cartridge element 200 being used during a testing and delivery event proximally and distally. The pinion gear 422 of the motor 421 drives a gear rack 424 in a direction parallel to the axis C of the cartridge element 200. The gear rack 424 is fixedly coupled to a connector 428 (see FIG. 22) that mechanically engages the connector 236 provided at the proximal end of the piston rod 234. As shown at FIG. 22, the connector 428 includes a projection that fits within the slot 237 of the piston rod connector 236.

The motor 431 functions to laterally eject the bottommost cartridge element 200 from the cartridge assembly 250 after the bottommost cartridge element 200 has been spent (e.g., has taken a fluid sample, has taken a predetermined number of fluid samples, has dispensed its drug dosage, etc.). The pinion gear 432 of the motor 431 engages a gear rack 436 of the arm 434 that moves back and forth along an axis E that is generally perpendicular relative to the axis C of the cartridge element 300. The gear arm 434 includes a ram 438 that engages the bottommost cartridge element 200 to laterally move the cartridge element 200 along the axis E such that the bottommost cartridge element 200 is disconnected from the remainder of the stack 250 and discharged from the monitoring and delivery system.

To initiate a fluid sample testing, the distal tip 102 of the analysis cell housing 104 is pressed against a test site on the patient. The first and second axial drive mechanisms 410, 420 are simultaneously initiated to drive the body 211 and the piston rod 234 of the cartridge element 200 in unison in a distal direction. The analysis cell 104 portion of the cartridge element 200 is held in a generally fixed location. Accordingly, driving the body 211 of the delivery arrangement 210 distally causes the flexible linkage 130 of the cartridge element 200 to compress and the skin piercing member 108 to enter the patient's tissue at a first depth suitable for drawing a fluid (e.g., blood) sample.

The fluid sample flows into the analysis cell housing 104 and an analyte (e.g., glucose) reading is generated at the electrodes 140, 142 and sent to the processor 320 of the monitoring and delivery system 300. During fluid sampling, the skin piercing member 108 is preferably driven distally into the patient's tissue and then retracted immediately to provide the fluid sample for analyte analysis within the analysis cell housing 104. After the analyte level has been determined, the processor 320 calculates the amount of drug (e.g., insulin) that should be dispensed to the patient based on the analyte reading.

Thereafter, the second axial drive mechanism 420 pulls the piston rod 234 proximally relative to the body 211 of the delivery arrangement 210. As the piston rod 234 is pulled back, the piston head (not shown) passes by and releases the flapper valve 238, thereby allowing the flapper valve 238 to open such that drug from the drug reservoir 222 is drawn into the piston chamber 224. Preferably, the piston rod 234 is pulled back a distance calculated to draw the desired dosage of drug from the drug reservoir 222 into the piston chamber 224.

Once the desired dosage of the drug has flowed into the piston chamber 224, the first and second axial drive mechanism 410, 420 simultaneously drive the body 211 and piston rod 234 as a unit in the distal direction. The body 211 engages the skin piercing member anchor 106. Accordingly, driving the body 211 distally while the analysis cell housing 104 is held fixed causes the flexible linkage 130 of the cartridge element 200 to compress, which causing the skin piercing member 108 to penetrate into the patient's tissue a depth suitable for delivering the drug into the tissue. Once the desired depth is reached, the movement of the body 211 in the distal direction is stopped, thereby stopping movement of the skin piercing member anchor 106 and the corresponding skin piercing member 108 in the distal direction.

Once the movement of the delivery arrangement body 211 stops, the second axial drive mechanism 420 continues to drive the piston rod 234 distally relative to the body 211 causing the drug within the piston chamber 224 to be forced from the piston chamber 224 through the interior of the skin piercing member 108 into the patient's tissue. As the drug is forced from the piston chamber 224, the flapper valve 238 prevents the drug from flowing from the piston chamber 224 back into the drug reservoir 222. Thereafter, the first and second axial drive mechanisms 410, 420 are again actuated to pull the delivery arrangement 210 and the piston rod 234 of the cartridge element 200 proximally in unison to cause the skin piercing member 108 to be withdrawn from the patient's tissue.

The delivery arrangement 210 also is coupled to a third drive mechanism 430 configured to drive the cartridge element 200 in a direction generally perpendicular to the axis C of the cartridge element 200. The third drive mechanism 430 can include a drive gear 432 and a drive arm 434 having a toothed section 436. The drive gear 432 interacts with the toothed section 436 of the drive arm 434 to move in a generally traverse direction to the movement of the other drive mechanisms 410, 420. In the example shown in FIG. 23, the drive arm 434 includes an abutment surface 437 and a flange 438 protruding outwardly from the abutment surface in the transverse direction. The flange 438 extends into the cavity 215 formed in the delivery arrangement 210 between the second rail 214. The abutment surface 437 presses against the exterior of the second rail 214 of the delivery arrangement 210.

Figure 24:
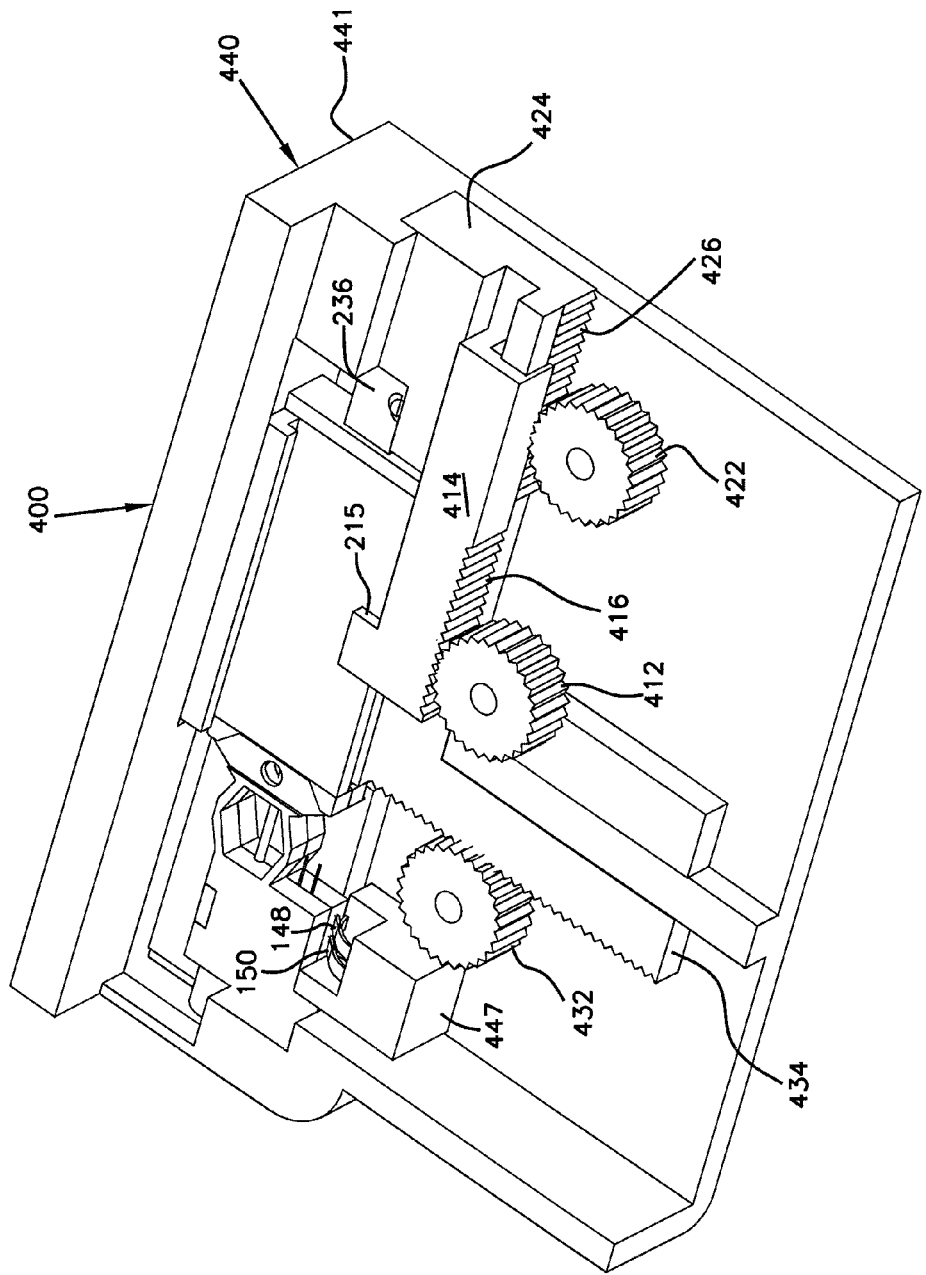
FIG. 24 is a top, isometric view of first, second, and third drive mechanisms and the cartridge element of FIG. 21 mounted on a base to form a drive system in accordance with the principles of the present disclosure.

Referring to FIGS. 24-29, the drive mechanisms 410, 420, 430 can be mounted onto a base 440 having a body 441 to form one example drive system 400 (FIGS. 24-26). The base body 441 has a first end 442, an opposite, second end 444, a first side 446, and an opposite, second side 448. A cartridge assembly 250 of one or more cartridge elements 200 can be loaded onto the drive system 400 to form a monitoring and delivery system (e.g., see FIGS. 27-29). The cartridge assembly 250 is loaded at the first side 446 of the body 441 such that each cartridge element 200 is oriented to extend between the first and second ends 442, 444 of the body 441 (see FIG. 25). The base body 441 can include a contact receiver 447 configured to contact the exposed portions of the electrode contacts 148, 150 protruding form the sensor module 100 of the bottommost cartridge element 200.

When the cartridge assembly 250 is loaded into the monitoring and delivery system, the bottommost cartridge element 200 of the stack is ready to be used. The first end 442 of the base body 441 defines an opening or slot 443 through which the distal end 102 of the sensor module 100 of the bottommost cartridge element 200 can access the test site on the patient. In one embodiment, the cartridge element 200 is positioned such that the distal end 102 of the sensor module 100 protrudes through the slot 443. In another embodiment, the distal end 102 is about flush with the first end 442 and the skin piercing member 108 protrudes through the slot 443 when moved into the extended position. It will be appreciated that the configuration of the slots 216 and rails 212, 214 provided on the body 211 of the delivery arrangement 210 enable the bottommost cartridge element 200 of the stack 250 to be slid along the axis C relative to the remainder of the cartridge elements.

After use of the bottommost cartridge element 200, the slot arrangement 216 of the body 211 allows the spent cartridge element 200 to be disconnected easily from the remainder of the cartridges and laterally ejected from the monitoring and delivery system. The first side 446 of the base body 441 defines a slot 445 extending between the first and second ends. Typically, the slot 445 of the first side 446 opens into the slot 443 defined in the first end 442 of the body 441. The third drive mechanism 430 pushes the delivery arrangement 210 of the bottommost cartridge element 200 in a transverse direction relative to the remainder of stacked cartridge elements 250 to disengage the bottommost cartridge element 200 from the stack and to eject the bottommost cartridge element 200 through the slot 445.

Referring to FIGS. 30-40, the drive system 400, metering electronics, and cartridge assembly 250 can be incorporated into an overall monitoring and delivery device. One example monitoring and delivery device (e.g., glucose monitoring and insulin delivery device) 500 shown in FIGS. 30-40 includes a device housing 510 having a top 501, a bottom 502, a first side 503, a second side 504, a front 505, and a rear 506. The top 501, a bottom 502, a first side 503, a second side 504, a front 505, and a rear 506 define a hollow interior 515 of the housing 510 in which the drive system 400 and metering electronics (e.g., the processor 320 of FIG. 3) can be installed. The metering electronics, such as a glucometer, are configured to determine analyte concentrations based on signals obtained from sensor modules installed within the device interior 515.

Figure 33:
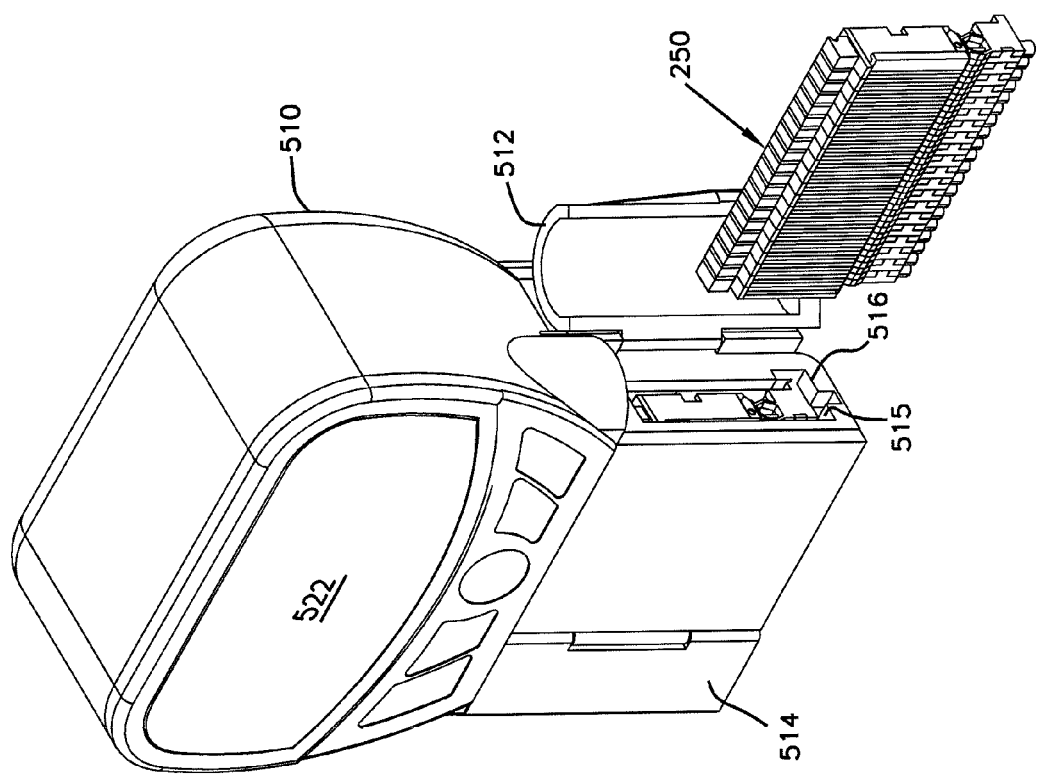
FIG. 33 is a top, isometric view of the monitoring and delivery device of FIG. 30 shown is a first door open and a cartridge assembly being loaded into an interior of the device via a first port in accordance with the principles of the present disclosure.
Figure 37:
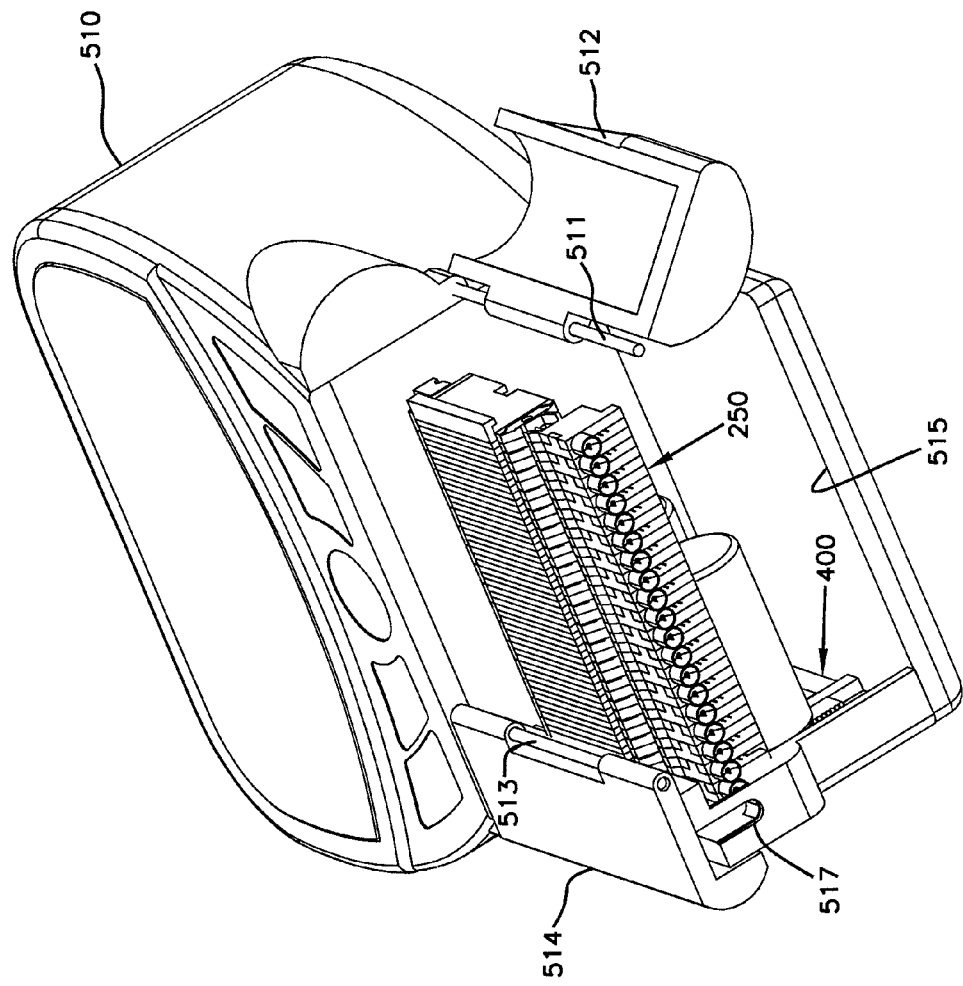
FIG. 37 is a bottom, isometric view of the monitoring and delivery device of FIG. 33 with a portion of the bottom and a portion of the front walls removed from the housing such that the cartridge assembly loaded within the interior of the housing is visible in accordance with the principles of the present disclosure.
Figure 38:
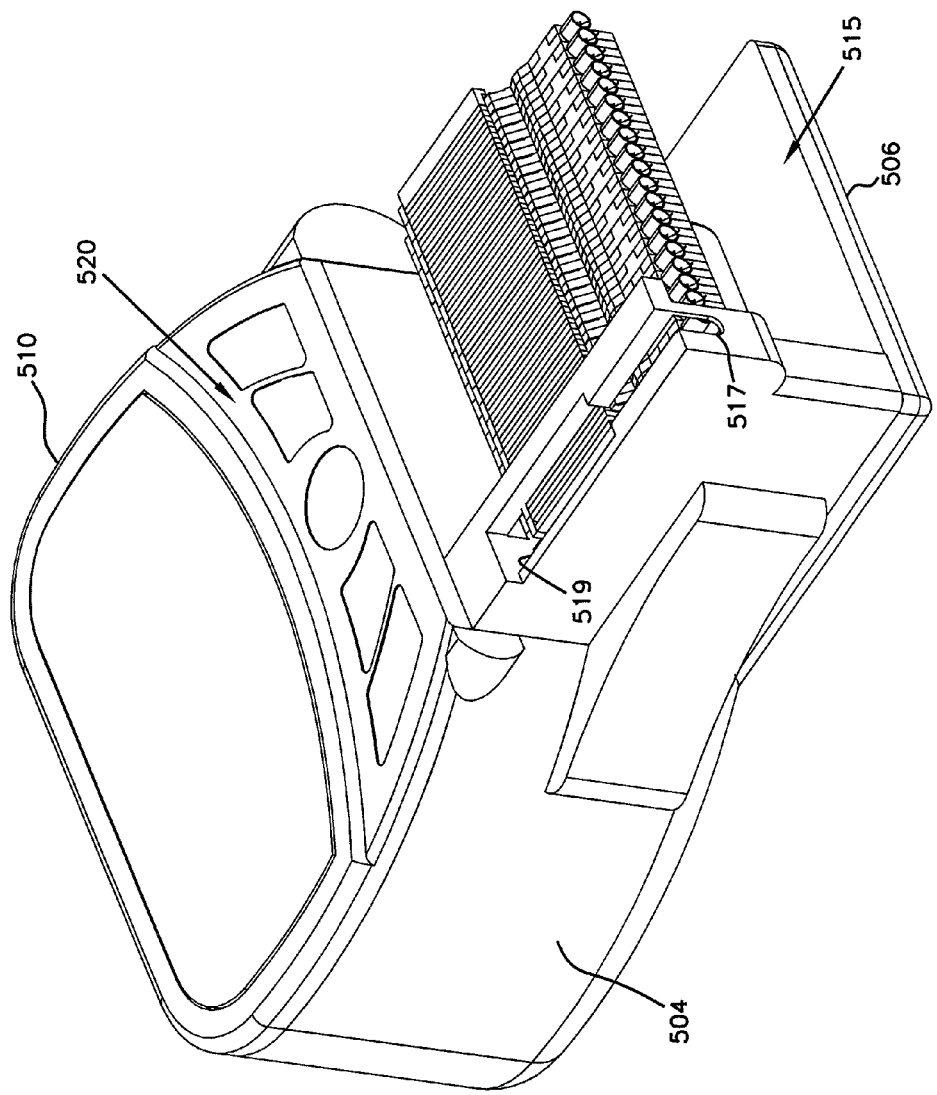
FIG. 38 is a top, isometric view of the monitoring and delivery device of FIG. 33 with portions of the front, first side, and bottom removed in accordance with the principles of the present disclosure.
Figure 39:
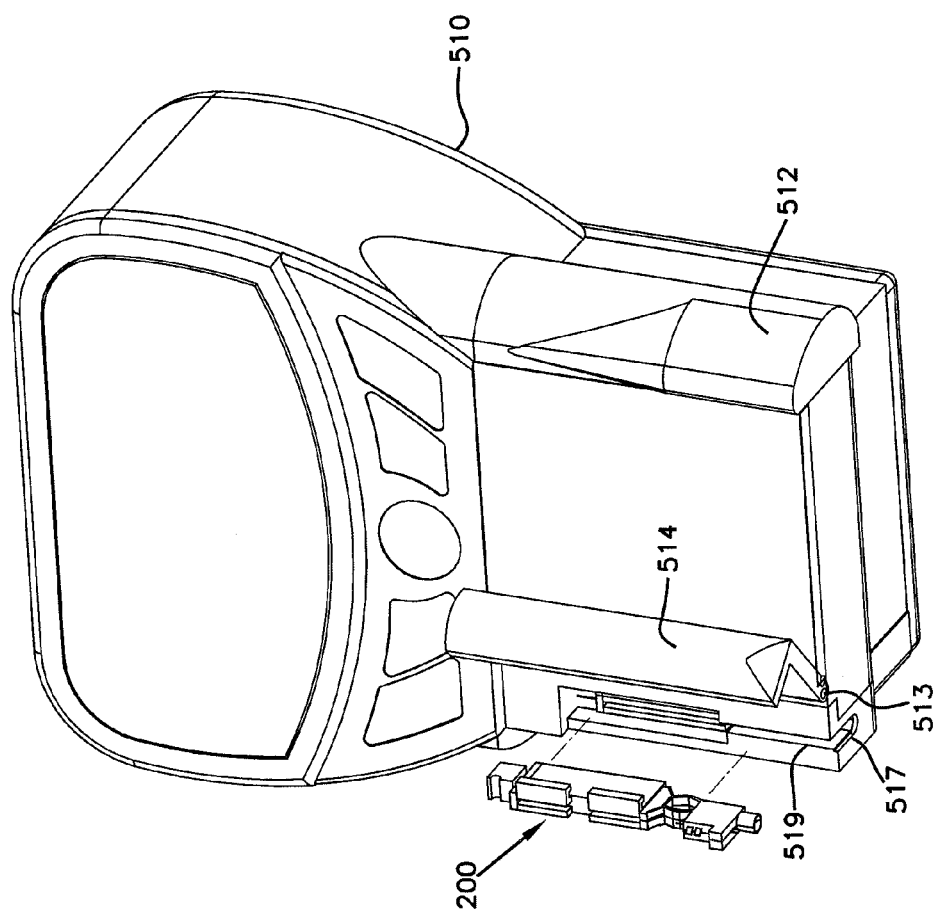
FIG. 39 is a front, bottom isometric view of a cartridge element being ejected from the monitoring and delivery device of FIG. 33 through a third port in accordance with the principles of the present disclosure.
Figure 40:
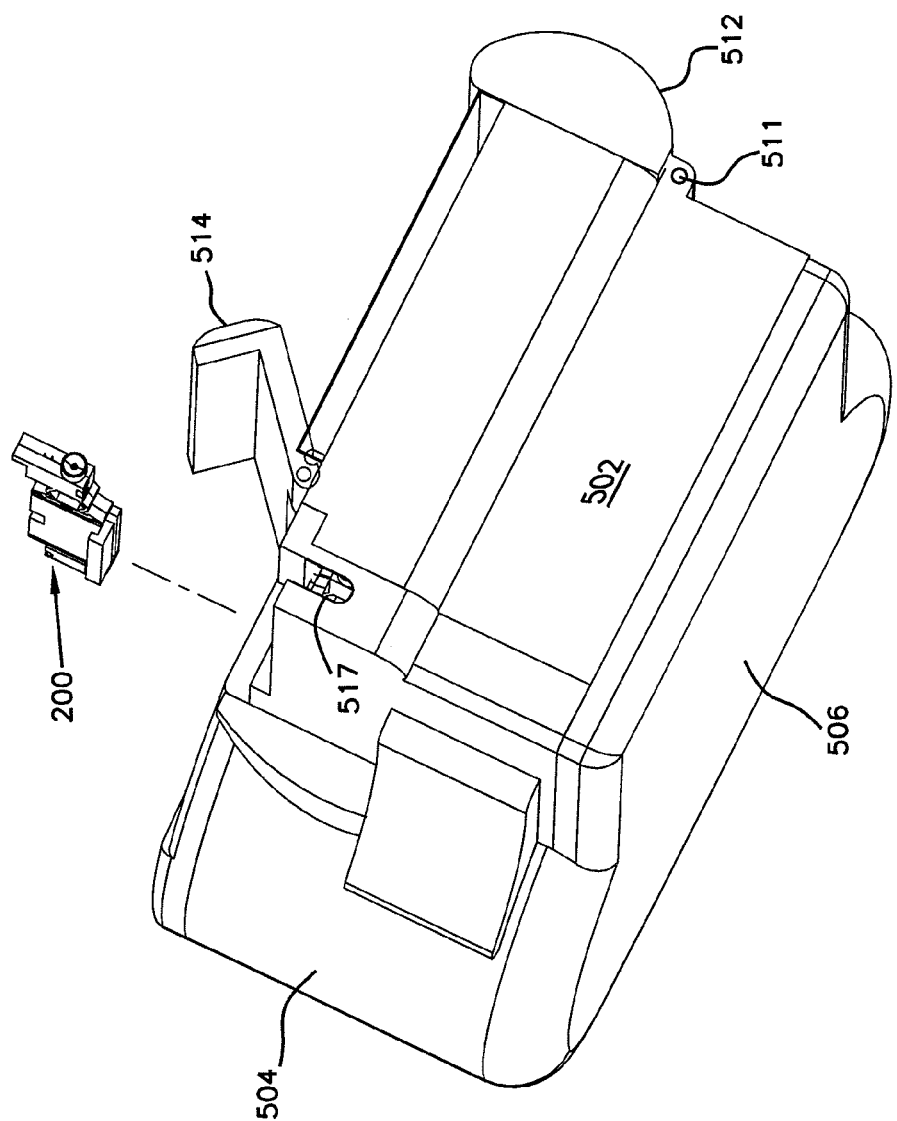
FIG. 40 is a bottom, isometric view of the cartridge element being ejected from the monitoring and delivery device of FIG. 39 in accordance with the principles of the present disclosure.

The first side 503 of the device housing 510 defines a first port 516 through which one or more cartridge assemblies 250 can be installed within the interior 515 of the housing 510 (e.g., see FIGS. 33-35). In general, the port 516 is sized and shaped to enable a cartridge assembly 250 to enter the interior 515 of the housing 510 through the port 516. In the example shown in FIG. 33, the port 516 is generally shaped to match a profile of the cartridge elements 200 of the cartridge assembly 250. A door 512 is configured to pivot about an axis 511 from a closed position (see FIG. 30), in which the door 512 covers the first port 516, to an open position (see FIG. 34), in which the door 512 allows access to the first port 516. In the example shown, the door 512 is generally curved. In other embodiments, the door 512 can be flat or any other suitable shape.

The cartridge assembly 250 is configured to be loaded into the monitoring and delivery device 500 by a patient. In general, when loaded into the monitoring and delivery device 500, the piston rods 234 of the delivery arrangements 210 are fully inserted within their corresponding piston chambers 224. As so positioned, the piston rods 234 engage the flapper valves 238 to hold the valves 238 in seated positions over the side ports 226. In this way, the drug contained in each of the delivery arrangements 210 is prevented from flowing from the drug reservoirs 222 to the piston chambers 224 until drug delivery is desired.

The cartridge assembly 250 is of sufficient size that it can be readily handled by a patient. However, since the sensor modules 100 of each cartridge element 200 in the assembly 250 are connected to the delivery arrangement 210 to form cartridge elements 200, the sensor modules 100 can be manufactured at smaller sizes since they never need to be handled individually by the patient. In one embodiment, the cartridge element 200 has a length of about 0.45 inches to about 0.75 inches, whereas the sensor modules 100 have lengths of about 0.6 inches to about 1.5 inches measured along the axis C and A, respectively, when the sensor modules 100 are arranged in the extended orientation. Multiple cartridge elements 200 are stacked or otherwise arranged in a cartridge assembly 250 to further facilitate handling of the cartridge elements 200.

When loaded into the device interior 515 through the first port 516, the cartridge assembly 250 is coupled to the drive system 400 and metering electronics contained within the housing 510. The sensor module 100 of the bottommost cartridge element 200 is connected to the metering electronics to facilitate transmission of analysis signals generated by the sensor module 100 to the metering electronics. For example, exposed contacts 148, 150 of the sensor module 100 of the bottommost cartridge element 200 can connect to the contact receiver 447 of the base body 441 of the drive system 400, which can be connected to the metering electronics.

The device housing 510 also includes a second port 517 defined in the bottom 502 (see FIG. 34). The second port 517 facilitates access between the patient test site and the distal end 102 of the sensor module 100 of the bottommost cartridge element 200 of a cartridge assembly 250 installed within the interior 515 of the housing 510. In use of the monitoring and delivery device 500, the distal end 102 of a cartridge element 200 being used to obtain and test a fluid sample projects through or is flush with the port 517 in the bottom 502 of the housing 510 to allow contact between the distal end 102 and the patient's tissue at the test site. In the example shown, the second port 517 remains exposed when the device 500 is not in use. In other embodiments, however, the device housing 510 can include a door or other cover for the second port 517 to protect the bottommost cartridge element 200 (e.g., from contaminants).

The device housing 510 also defines a third port 519 extending through the second side 504 of the housing 510 to provide access to the interior 515. The third port 519 is generally configured to enable one cartridge element 200 to be ejected from the interior 515 of the device housing 510 (e.g., see FIGS. 39 and 40). In the example shown in FIGS. 38-40, the third port 519 opens into the second port 517. In other embodiments, however, the third port 519 can be closed to the second port 517. A door 514 is configured to pivot about an axis 513 from a closed position (see FIG. 37), in which the door 514 covers the third port 519, to an open position (see FIG. 39), in which the door 514 allows access to the third port 519. In the example shown, the door 514 is generally L-shaped. In other embodiments, the door 514 can be flat or any other suitable shape.

The device housing 510 also includes a user interface 520 by which a user can input instructions and receives information from the device 500. In the example shown, the user interface 520 includes a display screen 522 on which data (e.g., an analyte concentration level, menu options, etc.) can be displayed arranged on the front 505 of the housing 510. The user interface 520 also includes input devices (e.g., buttons, knobs, toggle switches, track balls, dials, etc.) 524 and 526 arranged on the front 505 of the housing 510. The user input devices 524, 526 enable the user to program and/or actuate the drive system 400 and metering electronics within the housing 510. In other embodiments, the user interface 520 can include speakers to provide audible feedback to the user. Additional interface devices can include wireless output to computer, PDA or phone port, a battery charger port, a USB port, and a firewire port.

In certain embodiments, the monitoring and delivery device 500 is incorporated into a multi-purpose electronic device, such as a cell phone, PDA, or other such communication or data storage device.

Another example sensor module suitable for use with the delivery cartridge, driving system, and/or monitoring and delivery system is disclosed in copending application No. 61/114,829, filed Nov. 14, 2008, the disclosure of which is hereby incorporated by reference herein.

The above specification provides examples of how certain aspects may be put into practice. It will be appreciated that the aspects can be practiced in other ways than those specifically shown and described herein without departing from the spirit and scope of the present disclosure.

For example, an alternative method of monitoring and delivery includes inserting the piercing member into the skin at the depth prescribed for the drug (e.g., insulin) infusion. The piercing member has a laser drilled side port at a predetermined location proximal of the needle point. The laser hole is arranged in fluid communication with an annular chamber leading to the analysis cell.

The piercing member is inserted into the patient to about 100% of the depth required for drug infusion. When the piercing member reaches approximately 90% of the required tissue depth for drug infusion, the cannula of the piercing member is in fluid communication with the analysis cell through the side port. When the piercing member is arranged at 100% of the required depth, the side port is arranged distal of the entrance to the analysis cell. The side port is positioned within a narrower, occluding section of the passageway extending through the sensor housing. Accordingly, fluid is inhibited from passing from the piercing member through the side port.

When the piercing member is inserted at the required depth, the actuator (e.g., a pump) can be commanded to pull a fluid sample (e.g., a blood sample) from the patient up the cannula of the piercing member and past the side port. By then retracting the piercing member the distance of 10% of the insertion travel, the side port can be positioned within the annular chamber to align with the analysis cell. Subsequently, the actuator can be reversed to actively push a small fluid sample into the analysis cell through the side port.

After obtaining the fluid sample and analyzing the signals generated by the electrodes to determine an appropriate drug (e.g., insulin) dosage, the needle can then advance back to the 100% depth while the actuator draws an additional fluid sample (e.g., blood column) back up to the delivery arrangement 210 where the fluid sample is combined with the drug dose. Such a process eliminates dependence on capillary action and potentially reduces time required for analysis.

The invention claimed is:

1. A sensor cartridge element comprising:
a sensor module extending from a proximal end to a distal end, the sensor module including an analysis cell housing, a skin piercing member, and a skin piercing member anchor to which the skin piercing member is secured, the analysis cell housing defining an analysis cell and a sample passageway leading from the distal end of the sensor module to the analysis cell;
an electrode arrangement installed on the sensor module and arranged at least partially within the analysis cell of the sensor module, the electrode arrangement being configured to generate an electrical signal when exposed to a fluid sample collected in the analysis cell;
a delivery arrangement securely coupled to the sensor module, the delivery arrangement including a drug reservoir, a piston chamber, a piston rod disposed within the piston chamber, and a valve arrangement providing selective fluid communication between the drug reservoir and the piston chamber, the piston rod being disposed external of the drug reservoir, and the piston rod being coaxial with the skin piercing member, wherein the sensor cartridge is part of a sensor cartridge stack, and wherein the sensor cartridge is configured to couple to a second sensor cartridge element in the stack and a third sensor cartridge element in the stack.

2. The sensor cartridge element of claim 1, wherein the electrode arrangement includes a working electrode and a counter electrode.

3. The cartridge element of claim 1, wherein the sensor cartridge element includes a first rail that fits within a slot defined in the second sensor cartridge element, and wherein the sensor cartridge element includes a second rail that fits within a slot defined in the third sensor cartridge element.

4. The sensor cartridge element of claim 1, wherein the valve arrangement includes a flapper valve.

5. The sensor cartridge element of claim 1, wherein the valve arrangement provides fluid communication between the drug reservoir and the piston chamber when a piston rod is drawn in a first direction within the piston chamber sufficient to release the valve arrangement.

6. The sensor cartridge element of claim 1, further comprising a flexible linkage mechanically connecting the analysis cell housing to the skin piercing member anchor.

7. The sensor cartridge element of claim 1, wherein the piston chamber extends generally parallel to the drug reservoir.

8. The sensor cartridge element of claim 1, wherein the delivery arrangement includes an inner wall defining a port that provides fluid communication between the drug reservoir and the piston chamber.

9. The sensor cartridge element of claim 1, wherein the sensor cartridge element is one of a plurality of sensor cartridge elements disposed within an interior of a housing.

10. The sensor cartridge element of claim 9, wherein a controller is arranged within the interior of the housing, the controller including metering electronics.

11. The sensor cartridge element of claim 9, wherein the controller determines a portion of a drug dosage to be dispensed based on the electrical signal.

12. The sensor cartridge element of claim 9, wherein the controller determines when to inject a dosage based on the electrical signal.

13. The monitoring and delivery device of claim 9, wherein the controller determines a dosage size of insulin to be dispensed by the delivery arrangement.

14. The sensor cartridge element of claim 1, wherein the delivery arrangement includes a piston rod configured to move in a first direction to release the valve arrangement to provide fluid communication between the drug reservoir and the piston chamber to enable the portion of a drug to enter the piston chamber from the drug reservoir; and wherein the piston rod is further configured to move the piston rod in a second direction to expel the portion of the drug.

15. A device for sampling and dispensing, the device comprising
a housing, and a plurality of disposable cartridges, an actuator, and a controller disposed in the housing;
each cartridge comprising:
a sensor module extending from a proximal end to a distal end, the sensor module comprising a skin contact portion, a skin piercing element, an analysis cell housing defining a sample passageway, and an analysis cell in fluid communication with the piercing element, the analysis cell comprising at least first and second electrodes and adapted for analyzing the amount of analyte in a fluid sample, wherein the electrodes generate an electrical signal when exposed to a fluid sample collected in the analysis cell;
a drug reservoir; and
a delivery mechanism fluidly connecting the drug reservoir with the piercing element, the delivery mechanism comprising a piston chamber, a piston rod disposed within the piston chamber, and a valve arrangement providing selective fluid communication between the drug reservoir and the piston chamber, the piston rod being disposed external of the drug reservoir, and the piston rod being coaxial with the skin piercing element;
wherein the actuator is constructed to actuate the delivery mechanism;
and wherein the controller is operatively coupled with the actuator and capable of receiving signals from the analysis cell.

16. The device of claim 15, wherein each delivery mechanism is capable of delivering a selectively variable amount of drug from the drug reservoir.

17. The device of claim 15, wherein the controller is adapted to determine the amount of drug to be delivered by the delivery mechanism based on the signal from the analysis cell.

18. The device of claim 15, wherein each cartridge is slidably removable from the housing.

19. The device of claim 15, wherein the plurality of cartridges is disposed in the housing in a stacked arrangement.

20. The device of claim 19, wherein the stacked arrangement comprises an active end cartridge.

21. The device of claim 20, wherein the active end cartridge is slidably removable from the stacked arrangement.

22. The device of claim 20, wherein removing the active end cartridge exposes a next active end cartridge on the stacked arrangement until a last cartridge of the stacked arrangement is reached.

23. The device of claim 15, wherein each cartridge of the plurality of cartridges is a single use cartridge providing a single analysis of the analyte and a single delivery action.

* * * * *